United States Patent
Burn et al.

(10) Patent No.: US 7,812,323 B2
(45) Date of Patent: Oct. 12, 2010

(54) BRANCHED COMPOUNDS AND THEIR USE IN SENSORS

(75) Inventors: Paul Leslie Burn, Oxford (GB); Ifor David William Samuel, Fife (GB); Homar Barcena, Oxford (GB)

(73) Assignees: Isis Innovation Limited, Oxford (GB); The University Court Of The University Of St. Andrews, Fife (GB)

( * ) Notice: Subject to any disclaimer, the term of this patent is extended or adjusted under 35 U.S.C. 154(b) by 212 days.

(21) Appl. No.: 12/159,433

(22) PCT Filed: Jan. 5, 2007

(86) PCT No.: PCT/GB2007/000031

§ 371 (c)(1),
(2), (4) Date: Sep. 9, 2008

(87) PCT Pub. No.: WO2007/077456

PCT Pub. Date: Jul. 12, 2007

(65) Prior Publication Data

US 2009/0314957 A1  Dec. 24, 2009

(30) Foreign Application Priority Data

Jan. 6, 2006 (GB) .................. 0600249.7

(51) Int. Cl.
*G01J 1/58* (2006.01)
*C09K 11/06* (2006.01)
(52) U.S. Cl. ................ 250/458.1; 428/690; 252/301.16
(58) Field of Classification Search .............. 250/458.1, 250/459.1, 483.1, 484.2; 252/301.16; 257/40; 422/82.05; 428/690; 436/172

See application file for complete search history.

(56) References Cited

U.S. PATENT DOCUMENTS

| 5,150,006 A | 9/1992 | Van Slyke et al. |
|---|---|---|
| 5,157,261 A | 10/1992 | Grey et al. |
| 5,432,014 A | 7/1995 | Sano et al. |
| 6,083,634 A | 7/2000 | Shi |
| 6,312,809 B1 | 11/2001 | Crooks et al. |

(Continued)

FOREIGN PATENT DOCUMENTS

EP  1278061  1/2003

(Continued)

OTHER PUBLICATIONS

J. Lawrence et al., Optical Amplification in A First-Generation Dendritic Organic Semiconductor, 29 Optics Letters 869-871 (2004).

(Continued)

*Primary Examiner*—David P Porta
*Assistant Examiner*—Mark R Gaworecki
(74) *Attorney, Agent, or Firm*—Quarles & Brady LLP

(57) ABSTRACT

The invention provides sensors comprising one or more compounds of formulae (I) and (II):

$$[DENDRON^1]_p\text{-}CORE\text{-}[[X]_r\text{-}[DENDRON]_m]_n \quad (I)$$

$$[DENDRON^1]_p\text{-}[X]_r\text{-}[DENDRON]_q \quad (II)$$

wherein CORE, X, DENDRON, DENDRON$^1$, m, n, p, q and r are as defined herein. The optical (e.g. luminescent) and electronic properties of the compounds are capable of being altered by exposure to a number of different substances. The invention also provides the use of the compounds disclosed above in the sensing of substances, in particular explosives.

23 Claims, 4 Drawing Sheets

U.S. PATENT DOCUMENTS

| | | |
|---|---|---|
| 6,617,040 B2 | 9/2003 | Houser et al. |
| 2005/0196775 A1 | 9/2005 | Swager et al. |

FOREIGN PATENT DOCUMENTS

| | | |
|---|---|---|
| FR | 2861175 | 4/2005 |
| JP | 2004-277368 | 7/2004 |
| JP | 2005 220080 | 10/2005 |
| WO | WO 99/57222 | 11/1999 |
| WO | WO 01/77664 | 10/2001 |
| WO | WO 02/066552 | 8/2002 |
| WO | WO 02/067343 | 8/2002 |
| WO | WO 2005/073338 | 8/2005 |
| WO | WO 2005/124890 | 12/2005 |
| WO | WO 2006/035997 | 4/2006 |

OTHER PUBLICATIONS

E. Namdas et al., Photophysics of Fac-Tris (2-Phenylpyridine) Iridium (III) Cored . . . , 108 J. Phys. Chem. B 1570-1577 (2004).
F. Ilhan et al., Synthesis and Chemisensory Behavior of Anthracine Bisamide Derivatives, 16 Chem. Mater. 2978-2980 (2004).
R. Martinez-Manez et al., Fluorogenic and Chromogenic Chemosensors and Reagents For Anions, 103 Chem. Rev. 4419-4476 (2003).
V. Balzani et al., Luminescent Dendrimers. Recent Advances, 228 Topics in Current Chemistry 159-191 (2003).
PCT Written Opinion/Search Report in PCT/GB2007/000031, dated Aug. 25, 2007.
T. Gao et al., Detection and Classification of Volatile Organic Amines and Carboxylic Acids . . . , 17 Chem. Mater. 2904-2911 (2005).
G. Bergamini et al., Dendrimers Based on A Bis-Cyclam Core As Fluorescence Sensors For Metal Ions, J. Mater. Chem. (2005).
L. Svobodova et al., Properties of Mixed Alkanethiol-Dendrimer Layers and Their Applications In Biosensing, 63 Bioelectrochemistry 285-289 (2004).
N. Krasteva et al., Self-Assembled Gold Nanoparticle/Dendrimer Composite Films For Vapor Sensing Applications, 5 Nano Letters 551-555 (2002).
C. Kim et al., Ferrocene End-Capped Dendrimer: Synthesis and Application To CO Gas Sensor, 123 Synthetic Metals 493-496 (2001).
V. Balzani et al., Dendrimers As Fluorescent Sensors With Signal Amplification, Chemical Communications (2000).
V. Pugh et al., Optically Active BINOL Core-Based Phenyleneethynylene Dendrimers . . . , 66 J. Org. Chem 6136-6140 (2001).
A. Saxena et al., Fluoroalkylated Polysilane Film As A Chemosensor for Explosive Nitoaromatic Compounds, 17 Chem. Mater. 2181-2185 (2005).
C. Chang et al., Fluorescent Conjugated Polymer Films as TNT Chemosensor, 144 Synthetic Metals 297-301 (2004).
H. Sohn et al., Detection of Nitroaromatic Explosives Based on Photoluminescent Polymers Containing Metalloles, 125 J. Am. Chem. Soc. 3821-3830 (2003).
J. Morales et al., Studies on Conducting Polymer-Based Sensing Membranes With Tri-Iodide Organic . . . 105 Sensors and Actuators B 266-270 (2005).
G. Kannan et al., Adsorption Studies of Carbowax Coated Surface Acoustic Wave (SAW) Sensor . . . , 101 Sensors and Actuators B 328-334 (2004).
N. Guernion et al., The Synthesis of 3-Octadecly- and 3-docosylpyrrole, Their Polymerisation . . . , 128 Synthetic Metals 139-147 (2002).
G. Perez et al., Pore-Bridging Poly(dimethylsiloxane) Membranes As Selective Interfaces For Vapor-Phase Chemical Sensing, 76 Anal. Chem. 4137-4142 (2004).
D. Dermody et al., Chemically Grafted Polymeric Filters for Chemical Sensors: Hyperbranched . . . , 15 Langmuir 885-890 (1999).
L. Dorozhkin et al., Detection of Trace Amounts of Explosives and/or Explosive Related Compounds . . . , 99 Sensors and Actuators B 568-570 (2004).
X. Yang et al., Molecular Recognition and Self-Assembled Polymer Films for Vapor Phase Detection of Explosives, 54 Talanta 439-445 (2001).
V. Balzani et al., Dendrimers As Luminescent Hosts for Metal Cations and Organic Molecules, 6 C.R. Chimie 867-872 (2003).
T. Goodson et al., Optical Properties and Applications of Dendrimer-Metal Nanocomposites, 23 International Reviews In Physical Chemistry (2004) (abstract only).
P. Ceroni et al., Luminescence As A Tool to Investigate Dendrimer Properties, 30 Prog. Polym. Sci. 453-473 (2005).
L. Miller et al., "Vapoconductivity". Sorption of Organic Vapors Causes Large Increases In The Conductivity of a Dendrimer, 10 Chem. Mater. 1751-1754 (1998).
C. Chen et al., Recent Developments In Molecular Organic Electroluminescent Materials, 125 Macromol. Symp. 1-48 (1997).
M. Vasylyev et al., Dendritic Phosphonates and . . . , 347 Advanced Synthesis and Catalysis 39-44 (2005) (Abstract).
J. Markham et al., Conjugated Dendrimers, 2-4 Proceedings of SPIE (2004) (Abstract).
J. Markham et al., Nondispersive Hole Transport . . . , 81 Applied Physics Letters (2002) (Abstract).
Y. Totani et al., Organic Electroluminescent Device . . . , 67 JPN Kokai (2004).
Search report for priority application GB 0600249.7.

BRANCHED COMPOUNDS AND THEIR USE IN SENSORS

CROSS-REFERENCE TO RELATED APPLICATIONS

This application is a national phase application based on PCT/GB2007/000031 filed Jan. 5, 2007, and also claims priority based on GB 0600249.7 filed Jan. 6, 2006.

STATEMENT REGARDING FEDERALLY SPONSORED RESEARCH/DEVELOPMENT

Not applicable.

BACKGROUND OF THE INVENTION

1. Field of the Invention

The present invention relates to branched compounds and their use in sensors, particularly sensors for detecting the presence of explosives.

2. Description of the Prior Art

Semiconducting organic and organometallic (macro)molecules are promising materials for sensory devices because of their easily tunable electronic and optoelectronic properties, such as luminescence. Luminescence is the phenomenon by which light is emitted following excitation of molecules. While in theory an excited state should simply decay back to the ground state and in doing so release a photon, deactivation of the excited state can also occur by interaction with other species which will quench this luminescence. This effect can be utilised to detect analytes by measuring luminescence both before and after exposure to a substance and determining whether quenching of the luminescence has occurred.

Sensors which employ this change in luminescence in order to detect the presence of target analytes have been described previously, for example in WO-A-99/57222. This document describes polymers having characteristic luminescent lifetimes and quantum yields in isolation. However, when exposed to a target analyte which interacts with the electron distribution within the polymer after excitation, the luminescence properties change, and this can be detected as quenching of the luminescence. Analytes which can be detected by this method include any substances which cause at least partial quenching of the luminescence.

Another important example of how the optical properties of organic materials can be exploited is in devices that use amplified spontaneous emission (ASE), including lasers. In such a device, the active medium is energized, or pumped, by an external source such as light. This leads to a population inversion and stimulated emission occurs, amplifying the light coming out of the material. Analytes that interact with the active medium can alter its light amplifying properties and hence change its lasing behaviour.

There is an ongoing need to provide additional sensors which are capable of sensing different target analytes, or which are capable of sensing a plurality of target analytes, or which are capable of sensing target analytes at lower levels.

SUMMARY OF THE INVENTION

The invention provides a sensor comprising:
(i) a compound of formula (I):

$$[\text{DENDRON}^1]_p\text{-CORE-}[[X]_r\text{-}[\text{DENDRON}]_m]_n \quad (I)$$

wherein
n is an integer of from 1 to 10;
p is zero or an integer of from 1 to 9;
the sum of n and p is from 3 to 10;
CORE is a group providing at least (n+p) points of attachment, each point of attachment being bonded to one X, DENDRON or DENDRON$^1$ group, and wherein the bonds between CORE and at least three X, DENDRON or DENDRON$^1$ groups are not coplanar;
each r is independently zero or an integer of from 1 to 10;
each m is independently zero or 1, with the proviso that for every point of attachment, when r is zero then m is one, and when m is zero then r is greater than zero;
each $[X]_r$ group is the same or different, wherein:
when m is zero, then $-[X]_r$ is a terminal group, and each X, which is the same or different if r is greater than one, is a group selected from aryl, heteroaryl, vinylene, acetylene and iptycene groups and from planar metal complexes;
when m is 1, then $-[X]_r-$ is a linking group bonded to the CORE and terminating in a single bond to the first branching group of DENDRON, and each X, which is the same or different if r is greater than one, is a group selected from aryl, heteroaryl, vinylene, acetylene and iptycene groups and from planar metal complexes;
each DENDRON is the same or different and represents an at least partially conjugated dendritic molecular structure comprising at least one branching group and optionally at least one linking group, the branching groups being selected from aryl and heteroaryl groups and nitrogen atoms, and the linking groups being selected from aryl, heteroaryl, vinyl and acetylenyl groups, said branching groups being bonded to three or more groups, and said linking groups being bonded to two groups, said dendritic molecular structure terminating at its distal points in aryl and/or heteroaryl groups; and
each DENDRON$^1$, where present, represents an at least partially dendritic molecular structure; and
(ii) an excitation source and detector capable of measuring the electronic and/or optical properties of the compound of formula (I).

The invention further provides a sensor comprising:
(i) a compound of formula (II):

$$[\text{DENDRON}^1]_p\text{-}[X]_r\text{-}[\text{DENDRON}]_q \quad (II)$$

wherein:
q is an integer of from 1 to 10;
p is zero or an integer of from 1 to 9;
the sum of p and q is from 2 to 10;
r is zero or an integer of from 1 to 10;
$-[X]_r-$ is a linker group between the two or more DENDRON or DENDRON$^1$ groups and providing at least (p+q) points of attachment, each point of attachment being bonded to a DENDRON or DENDRON$^1$ group;
each X, which is the same or different if r is greater than one, represents a group selected from aryl, heteroaryl, vinylene and acetylene groups and from planar metal complexes;
each DENDRON is the same or different and represents an at least partially conjugated dendritic molecular structure comprising at least one branching group and optionally at least one linking group, the branching groups being selected from aryl and heteroaryl groups and nitrogen atoms, and the linking groups being selected from aryl, heteroaryl, vinyl and acetylenyl groups, said branching groups being bonded to three or more groups, and said linking groups being bonded to two groups, said dendritic molecular structure terminating at its distal points in aryl and/or heteroaryl groups; and each DENDRON$^1$, where present, represents an at least partially dendritic molecular structure; and (ii) an excitation source and detector capable of measuring the electronic and/or optical properties of the compound of formula (II).

The excitation source and detector are together capable of measuring the electronic and/or optical properties of the compound of formula (I) or formula (II). These properties differ in the presence of an analyte compared with the absence of the analyte. Thus, a change in the electronic and/or optical properties of the compound of formula (I) or formula (II), as measured by the excitation source and detector, can indicate the presence of the analyte.

In the sensors described above, in one embodiment the excitation source and detector are together capable of measuring an optical property of the compound of formula (I) or formula (II). Preferably this optical property is the luminescence of the compound. In this embodiment the luminescence of the compound of formula (I) or formula (II) changes in the presence of an analyte. If a difference is detected in the luminescence (as measured by the excitation source and detector) of the compound in the absence of an analyte and in the presence of a test substance, then the presence of the analyte in the test substance can be inferred. A suitable excitation source in this embodiment is a light source, which is capable of exciting the compound of formula (I) or formula (II) from a ground state to an excited state.

In an alternative embodiment the excitation source and detector are together capable of measuring an electronic property of the compound of formula (I) or formula (II). For example, the conductivity or resistivity of the compound can be measured. As with the embodiment described above, this electronic property changes in the presence of an analyte, and if a change is detected between the measurement in the absence of the analyte and in the presence of a test substance, then presence of the analyte in the test substance can be inferred. In this case, a suitable sensor is a field effect transistor (FET).

In a further embodiment, the excitation source and detector can be chosen such they measure both an electronic and an optical property of the compound of formula (I) or formula (II). In this embodiment multiple sources of excitation may be required in the excitation source, and the detector may require a number of separate sub-detectors, for example one sub-detector detecting the electronic property and another sub-detector detecting the optical property.

In the sensors described above, preferably the compound of formula (I) or formula (II) is present in the form of a film consisting essentially of said compound. As described above, the detector in the device is capable of detecting the change in electronic and/or optical properties of the compound of formula (I) or formula (II). When the compound of formula (I) or formula (II) is present in the form of a film consisting essentially of said compound, the electronic and/or optical properties of the film thus change upon exposure to the analyte, and the detector is capable of detecting this change in electronic and/or optical properties.

The invention also provides a sensor comprising a compound of formula (I) or formula (II) as defined above. In this embodiment the sensor additionally comprises an excitation source capable of causing a change in the optical properties of the compound and a detector capable of measuring said change.

There is also provided the use of a compound of formula (I) or formula (II) as defined above to detect the presence of a target analyte in a test substance.

The compounds used in the invention display a change in electronic and/or optical properties in the presence of an analyte compared with their electronic and/or optical properties in the absence of the analyte. Thus, the compounds used in the invention must be capable of changing their electronic and/or optical properties in order to be useful in the invention. More preferably the compounds are capable of displaying a change in their electronic properties or their optical properties in the presence of an analyte compared with these properties in the absence of the analyte. More preferably the compounds are capable of displaying a change in their optical properties in the presence of an analyte compared with their optical properties in the absence of the analyte. A preferred optical property which can change and be detected in the sensors and methods of the invention is the luminescence of the compounds. Clearly, in order to be useful in this way, the compounds must be luminescent either in the presence or absence of the analyte, or may be luminescent in both the presence and absence of the analyte but have a different level of luminescence in these scenarios.

Furthermore, the compounds used in the invention preferably contain at least one DENDRON and/or DENDRON$^1$ group which has an at least partially conjugated dendritic molecular structure. The compounds used in the invention are thus dendrimers, and are distinguished from linear polymeric compounds.

Furthermore, there is provided the use of a dendrimer to detect the presence of an explosive. Preferred dendrimers in this embodiment of the invention include the dendrimers of formula (I) or formula (II).

The invention further provides a method of detecting the presence of a target analyte in a test substance which method comprises:

(i) providing a compound of formula (I) or formula (II) as defined above and measuring the electronic and/or optical properties of said compound;

(ii) exposing said compound to the test substance and measuring the electronic and/or optical properties of the compound following exposure to the test substance;

(iii) comparing the electronic and/or optical properties obtained in step (ii) with those obtained in step (i); and (iv) determining that the target analyte is present if the electronic and/or optical properties obtained in step (ii) are different from those obtained in step (i).

As explained above, preferably either the change in electronic or optical properties are measured in the method, more preferably only the change in the optical properties are measured. A preferred optical property is the luminescence of the compound.

The target analyte is a substance which it is desired to detect and which is capable of altering the electronic and/or optical (e.g. luminescent) properties of the compound of formula (I) or formula (II). This capability may, for instance, arise from the electronic properties of the target analyte. In a preferred embodiment, the target analyte is a substance which it is desired to detect and which is capable of altering the luminescent properties of the compound of formula (I) or formula (II).

Examples of target analytes which can be detected are generally small molecules, for example molecules having a molecular weight of up to about 1000. Particular examples of the target analyte in this context include explosives, alkaloids, chemical warfare agents, taggants and analogues thereof.

The test substance is a substance which may or may not contain the target analyte to be detected.

The invention further provides novel compounds of formula (J) or (II) defined above. Preferred compounds of formula (I) are those wherein each r is zero or an integer of from 3 to 10, and each m is independently zero or 1, with the proviso that for every point of attachment, when r is zero then m is one, and when m is zero then r is an integer of from 3 to 10. More preferred features of the compounds of formula (I) are described below.

Preferred compounds of formula (II) are those wherein each r is an integer of from 2 to 10, and each X is the same or different and represents an aryl or heteroaryl group, the X groups being joined in series. More preferred features of the compounds of formula (II) are described below.

The compounds employed in the invention provide chromophores that can interact with or whose properties can be influenced by the target analytes, this being observable by the effect it has on the electronic or optical properties (e.g. on the luminescence) of the chromophores. In some embodiments, the analyte and the chromophore may interact directly with one another, for example the analyte may become bound to the chromophores, resulting in a change in electronic or optical properties. Most preferably this interaction between the analyte and the chromophore results in a detectable change in the luminescence of the chromophore. In other embodiments, the analyte and the chromophores may not interact directly, but instead the analyte may interact with another portion of the molecule containing the chromophore and this interaction may, in turn, result in a change in the electronic or optical properties of the chromophores. Again, in this embodiment it is preferred that the interaction (in this case between the analyte and another functional group on the molecule containing the chromophores) results in a detectable change in the luminescence of the chromophore.

In some circumstances, a chromophore may be excited in the presence of a target analyte that is an electron acceptor, such that once the exciton is formed on the chromophore the excited electron is transferred to the target analyte instead of decaying to the groundstate and simultaneously emitting a photon of light. Hence the luminescence of the chromophore is quenched. The requirements for such interactions are well known in the art and can be related to the redox potentials of the chromophore and the target analyte, and the energy gap between the highest and lowest unoccupied molecular orbitals.

For example, molecules which have a high electron affinity, for instance explosives molecules, will be attracted towards compounds used in the invention with chromophores having high electron density and which are easily oxidised in the excited state. When these molecules interact with the compounds used in the invention which comprise such chromophores, they cause quenching of the luminescence. This quenching effect (and hence reduction in the intensity of the luminescence) can thus be used to determine the presence of said molecules such as explosives. The target analytes sensed in the present invention can also change other properties of the luminescence. For example, these interactions may cause a change in the lifetime of the luminescence and/or wavelength of the luminescence. By detecting changes in lifetime and/or wavelength, presence of the target analyte can be detected. With regard to a change in lifetime of the luminescence, this could be measured using either time-domain or frequency-domain measurements.

As noted above, the target analytes which are to be sensed are generally small molecules, for example molecules having a molecular weight of up to about 1000. In particular, as noted above, the invention is useful in the detection of explosives, alkaloids, chemical warfare agents, taggants and analogues thereof. Exemplary explosives include 2,4,6-trinitrotoluene (TNT) and dinitrotoluene (DNT). Exemplary analogues of explosives include dinitrobenzene (DNB). Exemplary taggants include 2,3-dimethyl-2,3-dinitrobutane. Exemplary alkaloids include a whole host of drugs and drug metabolites such as cocaine and heroin, metabolites of steroids and the like. Exemplary chemical warfare agents include nerve agents such as sarin, VX and soman. However, the invention will clearly have wider applicability than for the exemplary target analytes discussed above. The structure of the compounds used in the invention can be manipulated in order to provide a different emissive response and hence allow for detection of other target analytes.

An advantage of the claimed compounds over known polymers for use in sensors is that their architecture can be more accurately controlled to provide better sensors. Furthermore, the conjugation length of the compounds of the invention is simpler to control than in known polymers, resulting in properties which are simpler to predict and manipulate.

A further advantage of the compounds used in the invention over known polymers is that they provide a greater density of chromophores per molecule, meaning that there is potential for a molecule to interact with one or more chromophores whose electronic and/or optical (e.g. luminescence) properties can be altered due to this interaction. As noted above, in one embodiment this alteration of the luminescent properties can be observed as a quenching of the luminescence, or in an alteration in the intensity and/or wavelength of the emission. The properties of the compounds can, of course, be tailored in order to interact more strongly with the target analyte which is to be measured by the sensor.

Similarly, the electronic properties of the compound may be adjusted to obtain preferential dendrimer-analyte (e.g. dendron-analyte) electrostatic interactions. For example, electron-rich polyaromatic dendrimers have an affinity towards electron-poor molecules such as TNT. Appending electron-donating groups onto the dendrimers should enhance TNT association or interaction, while electron-withdrawing groups should decrease TNT molecular recognition but improve recognition of more electron-rich target analytes such as N,N-dimethyltoluidine.

Without wishing to be bound by theory, it is postulated that the internal free volume available around the chromophores of the above compounds allows for binding of target analyte molecules. When said target analyte molecules bind to the compounds used in the invention, they cause a measurable change in the luminescent properties, e.g. quenching of the luminescence. By noting and recording the change in luminescence after exposure to the target analyte, the presence of the target analyte can be determined. The binding with the target analyte can be reversible.

The claimed sensors also show advantages because the compounds used in said sensors can be designed to exhibit a high degree of selectivity towards target analytes through electronic and structural modifications. For example, the number and size of the cavities may be changed by using larger units in the dendrons or adopting higher generations; this would enhance specificity for target analytes of different sizes. The same operation leads to more porous films, which allow target analytes to diffuse faster into the film to give a

DETAILED DESCRIPTION OF THE INVENTION

Figure 1:
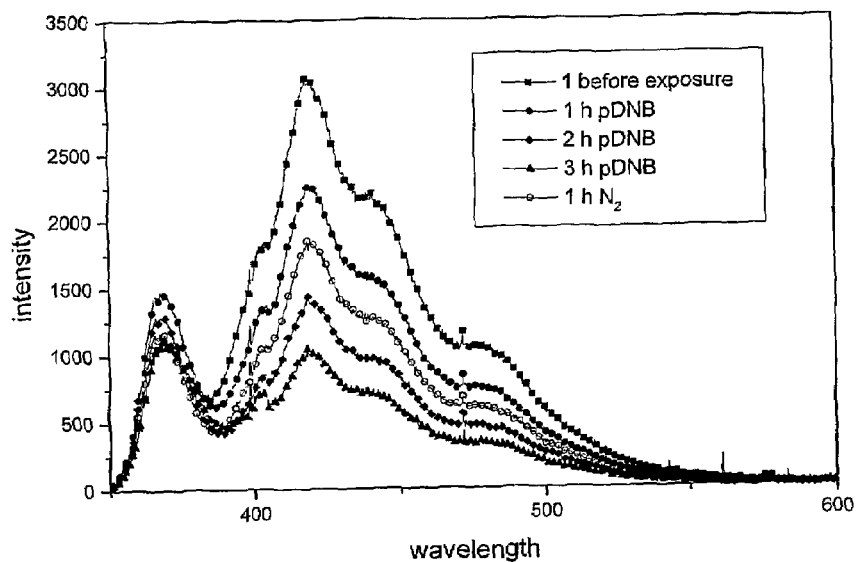
FIG. 1 shows the photoluminescence of a compound of the invention (compound 1) before exposure to p-dinitrobenzene (pDNB), and also at a number of different time periods after exposure to pDNB.
Figure 2:
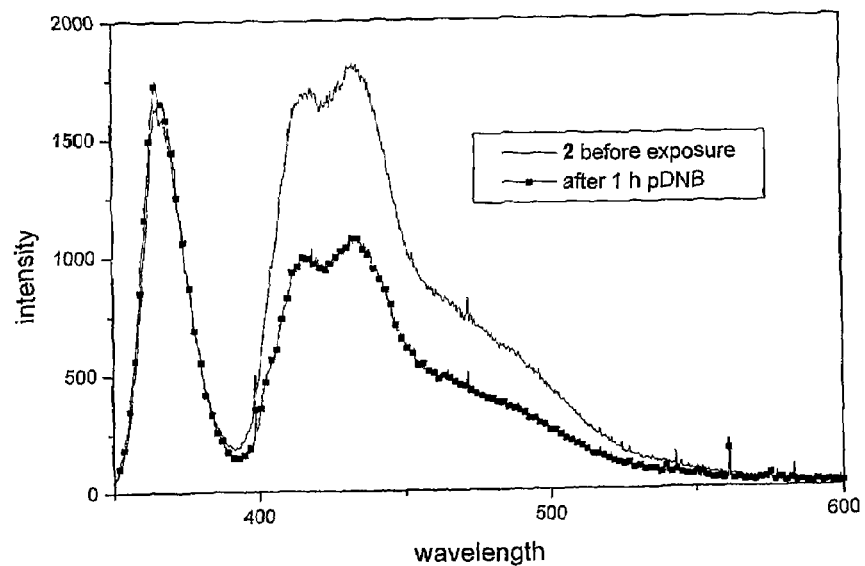
FIG. 2 shows similar photoluminescence spectra for compound 2 of the invention.
Figure 3:
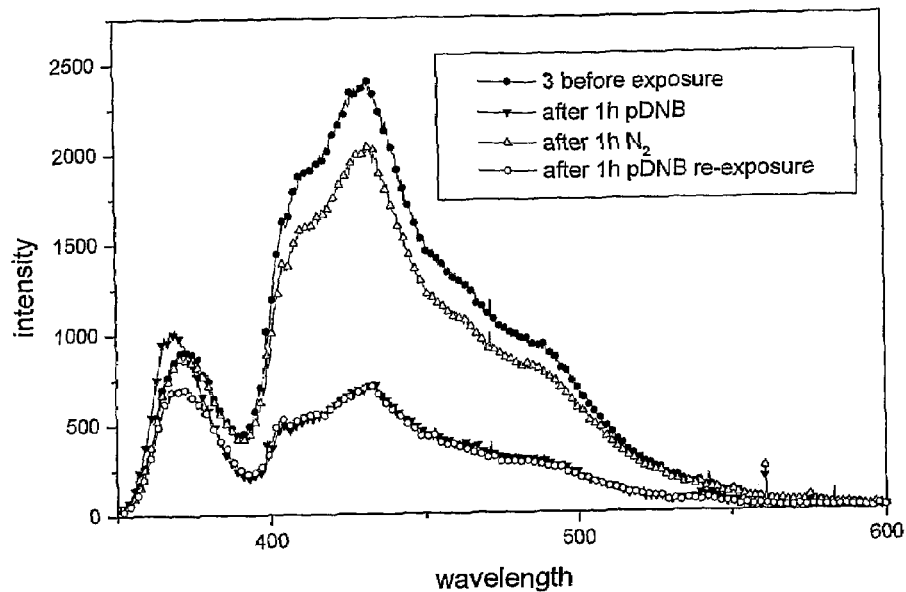
FIG. 3 shows similar photoluminescence spectra for compound 3 of the invention.
Figure 4:
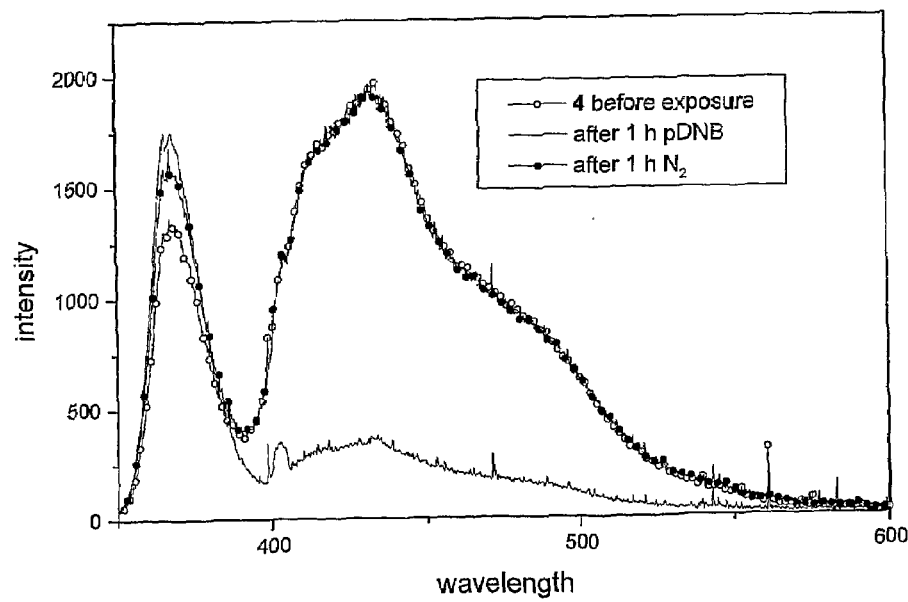
FIG. 4 shows similar photoluminescence spectra for compound 5 of the invention.

As used herein the term $C_{1-10}$ alkyl is a linear or branched alkyl group or moiety containing from 1 to 10 carbon atoms such as a $C_{1-4}$ or $C_{1-6}$ or $C_{1-8}$ alkyl group or moiety. Examples of $C_{1-4}$ alkyl groups and moieties include methyl, ethyl, n-propyl, i-propyl, n-butyl, i-butyl and t-butyl. For the avoidance of doubt, where two alkyl moieties are present in a group, the alkyl moieties may be the same or different.

As used herein, a $C_{2-6}$ alkenyl group or moiety is a linear or branched alkenyl group or moiety containing from 2 to 6 carbon atoms respectively such as a $C_{2-4}$ alkenyl group or moiety. For the avoidance of doubt, where two or more alkenyl moieties are present in a group, the alkenyl moieties may be the same or different.

As used herein, a halogen is typically chlorine, fluorine, bromine or iodine. It is preferably chlorine, fluorine or bromine, more preferably fluorine.

As used herein, the term hydroxyalkyl represents a said alkyl group bearing at least one (more preferably one) hydroxy group.

As used herein the term amino represents a group of formula —$NH_2$. The term $C_{1-10}$ alkylamino represents a group of formula —NHR' wherein R' is a $C_{1-10}$ alkyl group, preferably a $C_{1-8}$ alkyl group, as defined previously. The term di($C_{1-10}$)alkylamino represents a group of formula —NR'R" wherein R' and R" are the same or different and represent $C_{1-10}$ alkyl groups, preferably $C_{1-8}$ alkyl groups, as defined previously. As used herein the term amido represents a group of formula —C(O)NR'R" wherein R' and R" are the same or different and are selected from hydrogen and $C_{1-10}$ alkyl groups, more preferably from hydrogen and $C_{1-8}$ alkyl groups as defined previously.

As used herein the term aryl refers to $C_{6-30}$ aryl groups which may be mono- or polycyclic. Suitable polycyclic aryl groups include fluorenyl, anthracenyl, naphthyl, perylene, pyrene, phenanthrene, coronene and benzopyrene, along with other similar aromatic hydrocarbons. Preferred aryl groups include phenyl. Preferred polycyclic aryl groups include fluorenyl, anthracenyl and naphthyl, particularly fluorenyl and naphthyl, more particularly fluorenyl. Other preferred aryl groups include pyrene and perylene groups.

An aryl group can be unsubstituted or substituted at any position. Unless otherwise stated, it carries 0, 1, 2, 3 or 4 substituents. Preferred substituents on an aryl group include halogen, $C_{1-10}$ alkyl, $C_{2-10}$ alkenyl, —C(O)R wherein R is hydrogen or $C_{1-10}$ alkyl, —$CO_2$R wherein R is hydrogen or $C_{1-10}$ alkyl, hydroxy, $C_{1-10}$ alkoxy, $C_{2-10}$ alkenyloxy, $C_{1-10}$ alkylthio, $C_{2-10}$ alkenylthio, $C_{1-10}$ haloalkyl, $C_{2-10}$ haloalkenyl, $C_{1-10}$ haloalkoxy, $C_{2-10}$ haloalkenyloxy, amino, $C_{1-10}$ alkylamino, di($C_{1-10}$)alkylamino, $C_{6-14}$ aryloxy, —$O_2$SR or —$SiR_3$ wherein each R is the same or different and represents hydrogen, $C_{1-10}$ alkyl or $C_{2-10}$ alkenyl, $C_{6-14}$ arylthio, $C_{6-14}$ aryl and 5- to 10-membered heteroaryl, and wherein the substituents are themselves unsubstituted or substituted, or fluoro. Other suitable substituents include hydroxy($C_{1-10}$) alkyl and hydroxyhalo($C_{1-10}$)alkyl groups, for example hydroxy($C_{1-4}$)alkyl and hydroxyhalo($C_{1-4}$)alkyl groups.

When the substituents are themselves substituted, suitable substituents on the substituents include 1, 2, 3 or 4 groups selected from $C_{1-10}$ alkyl, $C_{2-10}$ alkenyl, $C_{1-10}$ alkoxy, $C_{2-10}$ alkenyloxy, hydroxy and halogen, particularly suitable are 1 or 2 groups selected from $C_{1-8}$ alkyl, $C_{2-8}$ alkenyl, $C_{1-8}$ alkoxy and $C_{2-8}$ alkenyloxy.

Most preferred substituents on aryl groups according to the invention include $C_{1-10}$ alkyl and $C_{1-10}$ alkoxy groups, such as $C_{1-8}$ alkyl and $C_{1-8}$ alkoxy groups. The substituents are preferably themselves unsubstituted.

As used herein, a heteroaryl group is typically a 5- to 30-membered aromatic ring, for example as a 5- to 10-membered ring, such as a 5- or 6-membered ring, containing at least one heteroatom, for example 1, 2 or 3 heteroatoms, selected from O, S and N. Examples include pyridyl, pyrazinyl, pyrimidinyl, pyridazinyl, furanyl, thienyl, pyrrolyl, oxadiazolyl, thiadiazolyl, thiazolyl, imidazolyl, oxazolyl, benzofuranyl, indolyl, indazolyl, carbazolyl, purinyl, cinnolinyl, quinoxalinyl, naphthyridinyl, benzimidazolyl, benzoxazolyl, quinolinyl, quinazolinyl and isoquinolinyl.

When the heteroaryl group is a monocyclic heteroaryl group, preferred groups include thiophenyl, pyrrolyl, pyridyl, furanyl and oxadiazolyl.

As used herein, references to a heteroaryl group include fused ring systems in which a heteroaryl group is fused to an aryl group. When the heteroaryl group is such a fused heteroaryl group, preferred examples are fused ring systems wherein a 5- to 6-membered heteroaryl group is fused to one or two phenyl groups. Examples of such fused ring systems are benzofuranyl, benzopyranyl, cinnolinyl, carbazolyl, benzotriazolyl, phenanthridinyl, indolyl, indazolyl, benzimidazolyl, benzoxazolyl, quinolinyl, quinazolinyl and isoquinolinyl moieties, as well as even larger polycyclic groups such as porphyrins. When a heteroaryl ring is a polycyclic group, preferred groups include carbazolyl, as well as much larger heteroaryl groups such as porphyrins.

A heteroaryl group may be unsubstituted or substituted at any position. Unless otherwise stated, it carries 0, 1, 2 or 3 substituents. Preferred substituents on a heteroaryl group include those listed above in relation to aryl groups. When a heteroaryl group is substituted by a $C_{6-14}$ aryl group or by a 5- to 10-membered heteroaryl group, these substituents are themselves unsubstituted or substituted by one or more substituents selected from $C_{1-15}$ alkyl, $C_{2-15}$ alkenyl, $C_{1-15}$ alkoxy and $C_{2-15}$ alkenyloxy. When a heteroaryl group is substituted by groups other than $C_{6-14}$ aryl groups or 5- to 10-membered heteroaryl groups, the substituents are themselves preferably unsubstituted.

As used herein, an alkoxy group is typically a said alkyl group attached to an oxygen atom. Similarly, alkenyloxy groups and aryloxy groups are typically a said alkenyl group or aryl group respectively attached to an oxygen atom. An alkylthio group is typically a said alkyl group attached to a thio group. Similarly, alkenylthio groups and arylthio groups are typically a said alkenyl group or aryl group respectively attached to a thio group. A haloalkyl or haloalkoxy group is typically a said alkyl or alkoxy group substituted by one or more said halogen atoms. Typically, each carbon atom of said group is substituted by one or more halogen atoms, with the maximum number of halogen atoms being the number required to bring the total valency of the carbon atom to four. Haloalkyl and haloalkoxy groups include perhaloalkyl and perhaloalkoxy groups such as —$CX_3$, —$CX_2CX_3$ and —$OCX_3$ wherein X is a said halogen atom, for example chlorine or fluorine, as well as longer alkyl and/or alkoxy chains such as $C_{2-6}$ chains substituted by one or more halogen atoms. In the context of haloalkyl and haloalkoxy groups, a preferred halogen atom is fluorine.

Haloaryl groups are, by analogy, typically a said aryl group substituted by one or more said halogen atoms. Typically, it is substituted by 1, 2 or 3 said halogen atoms.

Hydroxyhaloalkyl groups represent haloalkyl groups as described above wherein the alkyl group is further substituted by at least one (more preferably one) hydroxy group.

As noted earlier, the invention can utilise compounds of formula (I) or formula (II). The compounds of these two formulae are similar, except that formula (I) requires that the CORE provides three-dimensionality to the molecule whereas formula (II) provides a "core" of X groups which need not provide three-dimensionality, and which may instead be a more planar structure.

For both formula (I) and formula (II), at least one moiety within the compound must be luminescent. This may be one or more of the chains extending from the central CORE (where present), may be the CORE itself, may be one or more of the DENDRON groups, or one or more of the X groups (where present). The luminescent moiety or moieties are called chromophores. In addition, $DENDRON^1$ may or may not contain a luminescent chromophore.

There may be more than one chromophore providing luminescence within the molecule, for example all DENDRON groups may be luminescent, or all moieties within the molecule may be luminescent. The chromophores may all be in the same area of the compound, for example all chromophores may be present on a single DENDRON, with other parts of the molecule, e.g. $DENDRON^1$ being non-emissive. The emissive properties of the chromophore can be manipulated by appropriate design of the compound. For example, the length of the chromophore can be manipulated in order to achieve different emissive properties. However, in order to act as a sensor for a particular target analyte, the compound must have at least one chromophore which is responsive to the target analyte which is to be tested for.

It will be appreciated that the luminescence provided by the compounds can be either fluorescent or phosphorescent depending on the nature of the compound. Furthermore, the luminescence may result from the CORE and/or X groups and/or DENDRON groups.

In some embodiments phosphorescence is preferred because the lifetimes of excited states are easier to measure than for fluorescence, and because the low radiative rate of these materials makes them more sensitive to changes in non-radiative rate.

On the other hand, phosphorescence may in some circumstances be less preferred in view of the fact that oxygen may quench the excited state.

As examples of these two types of luminescence, when an organometallic CORE is used, for example employing a CORE using a heavy d-block metal, the compound is likely to be phosphorescent. The use of other metals or metal containing groups, e.g. $AlQ_3$, or the use of organic cores, is likely to result in a fluorescent compound.

If the complex is to be phosphorescent, this will generally be achieved using a central organometallic CORE in the case of formula (I), or organometallic groups within the X groups in the case of formula (II). To ensure a good signal, it is preferable to ensure that quenching of the phosphorescence by the remaining chromophores in the structure is minimised or avoided. This can be done by ensuring that the triplet energies of the groups which are attached to the CORE (for formula (I)) or X groups (for formula (II)) are higher (preferably significantly higher) than the emissive energy of the CORE. If the triplet energy of these groups is lower than or sometimes even just close to the emissive energy of the CORE then undesirable quenching of the phosphorescence may arise.

Compounds of formula (I) and (II) may optionally comprise $DENDRON^1$ groups bonded to the central CORE or X groups. $DENDRON^1$ groups need not contain chromophores, and are simply used to replace one or more X and/or DENDRON groups around the central CORE. $DENDRON^1$ groups can contain conjugated chromophores, but preferably the $DENDRON^1$ groups are non-conjugated.

$DENDRON^1$ can in general be any type of dendrimer other than those defined by DENDRON. For example, each $DENDRON^1$, which may be the same or different if p is greater than one, can be a PANAM-type dendron, or can be a Frechet-type DENDRON as shown for example in Chem. Rev., 2001, 101, 3819-3867. It can be an at least partially conjugated or a non-conjugated dendron. For at least partially conjugated dendrons for example, the links between the branching points in $DENDRON^1$ may be non-conjugated yet the $DENDRON^1$ group may still contain chromophores, e.g. at their distal end. Furthermore, $DENDRON^1$ can be substituted as for DENDRON. As with DENDRON, $DENDRON^1$ can provide at least one branching group and optionally linking groups. It can be of any generation, although it is preferably a first to sixth generation dendrimer. In one embodiment, $DENDRON^1$ is an at least partially dendritic molecular structure comprising at least one branching group and optionally at least one linking group, the branching groups being selected from aryl and heteroaryl groups and nitrogen atoms, and the linking groups being selected from aryl, heteroaryl, alkyleneoxy, vinyl and acetylenyl groups, said at least one branching group being bonded to three or more groups, and said at least one linking group being bonded to two groups, said dendritic molecular structure terminating at its distal points in aryl and/or heteroaryl groups.

Compounds of formula (I) and formula (II) may both contain one or more metal complexes within the structure, in particular as part of the CORE (for formula (I)) or X groups (for formula (II)). As discussed earlier, formula (I) requires that the CORE provides three-dimensionality, and the metal complex or complexes will therefore be chosen in order to provide this, e.g. through the use of an octagonal, tetrahedral or trigonal bipyramidal coordinated metal. This will discussed in more detail below. Similarly, formula (II) does not require that the group -[X]$_r$- provides three-dimensionality, and in fact it is preferred that the -[X]$_r$- group in compounds of formula (II) is planar. This can be achieved through the selection of planar metal complexes, e.g. by choosing metals with a square planar or trigonal planar coordination. Again, this will be discussed later. For compounds of both formula (I) and formula (II) it is preferred that the complex is diamagnetic rather than paramagnetic. Paramagnetic complexes tend to result in unwanted quenching of luminescence.

As a general point, the X and DENDRON groups in the compounds may or may not be the same. By employing the same groups it may be possible to increase the sensitivity and accuracy of a sensor employing the compound by increasing the number of chromophores available for the target analyte to bind to or to interact with (e.g. via a functional group on the compound, as discussed earlier. However, by employing different groups which provide different chromophores, it may be possible for one compound to allow for detection of more than one target analyte.

These two types of compound will now be discussed separately in more detail.

Compounds of Formula (I):

Compounds of formula (I) comprise a central CORE about which a number of chains extend.

At least one moiety within the compound must be luminescent, and this may be one or more of the chains extending from the central CORE, may be the CORE itself, may be one or more of the DENDRON or $DENDRON^1$ groups, or one or more of the X groups (where present). The luminescent moiety or moieties are called chromophores. There may be more than one chromophore providing luminescence within the molecule, for example all DENDRON groups may be luminescent, or all moieties within the molecule may be luminescent. The chromophores may all be in the same area of the compound, for example all chromophores may be present on a single DENDRON, with other parts of the molecule, e.g. $DENDRON^1$ being non-emissive. The emissive properties of the chromophore can be manipulated by appropriate design of the compound. For example, the length of the chromophore can be manipulated in order to achieve different emissive properties. However, in order to act as a sensor, the compound must have at least one chromophore which is responsive to the target analyte which is to be tested for. It is preferred that the chromophore is part of CORE, and/or DENDRON and/or X.

The sum of n and p defines the number of chains extending from the CORE, and optionally via X groups, and ranges from 3 to 10. Integer n determines the number of -$[X]_r$-DENDRON groups present, and is preferably from 1 to 10, more preferably from 1 to 6, more preferably from 2 to 6, e.g. 4. The subscript p defines the number of $DENDRON^1$ groups present and is zero or an integer of from 1 to 9, preferably zero, 1 or 2, more preferably zero or 1, and most preferably zero.

The CORE of the compounds of formula (I) is the central group which provides at least as many points of attachment as there are -$[X]_r$-DENDRON and $DENDRON^1$ groups to attach to the CORE. While CORE is described as providing at least n+p points of attachment to which X, DENDRON or $DENDRON^1$ groups are attached, CORE may of course contain a number of additional potential points of attachment which are not bonded to X, DENDRON or $DENDRON^1$ groups. What is necessary is that there are at least three bonds between CORE and three X, DENDRON and/or $DENDRON^1$ groups which do not fall within the same plane. Thus, the CORE is a group which provides three-dimensionality to the compound by ensuring that not all of the groups extending from the CORE are coplanar. By choosing this arrangement it is possible to provide cavities within the structure of the compound wherein a target analyte can bind. Furthermore, by choosing this arrangement it is possible to reduce the intermolecular interactions that lead to quenching of the luminescence of the chromophores, for example π-stacking of the chromophores. This has the effect of reducing interactions between the luminescent chromophores both on adjacent compounds and within the same compound.

Suitable COREs are groups which inherently provide attachment points which will lead to three-dimensionality. By "inherently" it is meant that regardless of steric effects caused by the X, DENDRON and $DENDRON^1$ groups which may be present, the bonds extending from CORE to at least three X, DENDRON or $DENDRON^1$ groups are not co-planar.

The nature of the CORE is not particularly critical, and it can simply be chosen in order to provide the requisite number of points of attachment for the X, DENDRON and $DENDRON^1$ groups. Particularly suitable COREs include organometallic cores, organic cores and other inorganic cores which provide three-dimensionality.

Exemplary inorganic cores include silicon atoms, silsesquioxane and cyclic phosphazene groups.

Exemplary organic cores include carbon atoms, adamantane, silane cores such as tetraphenylsilane and spiro compounds such as spirofluorenes.

Exemplary organometallic cores include three dimensional metal complexes, e.g. tetrahedral, octahedral and trigonal bipyramidal complexes. Suitable metals include lanthanide metals, for example cerium, samarium, europium, terbium, dysprosium, thulium, erbium and neodymium. Other suitable metals include d-block metals, especially those in rows 2 and 3, such as iridium, platinum, rhodium, osmium, ruthenium, rhenium, scandium, chromium, manganese, iron, cobalt, nickel and copper. As noted earlier, preferably the complex is itself diamagnetic, rather than paramagnetic. Further metals include metals from Groups 1A, IIA, IIB, IIIB, such as lithium, beryllium, magnesium, zinc, aluminum, gallium and indium. Preferred organometallic cores include osmium, ruthenium, rhenium, europium, terbium, platinum, and iridium.

In one aspect of the invention CORE may be represented as a complex of the following formula:

$$M[Z\text{-}]_s Y_t$$

wherein M is a metal cation, such as those listed above, each [Z-], which are the same or different, is a coordinating group attached to a single bond in which CORE terminates, each Y, which may be the same or different, is a coordinating group, s is an integer of 3 or above and t is 0 or an integer, the sum of (a.s)+(b.t) being equal to the number of coordination sites available on M, wherein a is the number of coordination sites on [Z-] and b is the number of coordination sites on Y. Preferably s is from one to three. Preferably t is zero, one or two.

The single bond in the or each [Z-] moiety, being a bond in which CORE terminates, connects to X, to DENDRON or to $DENDRON^1$. There are at least three groups extending from the CORE, hence s is an integer of 3 or more. The coordinating groups Y, when present, are neutral or charged chelated ligands which are not attached to dendrons and which serve to fulfil the coordination requirements of the metal cation. Suitable substituents Y, for rhenium in particular, include CO and halogen such as chlorine. For iridium dendrimers, the part of the ligands attached to the metal is preferably a nitrogen-containing heteroaryl, for example pyridine, attached to a hetero(aryl) where aryl can be a fused ring system, for example substituted or unsubstituted phenyl or benzothiophene.

Suitable coordinating groups for the f-block metals include oxygen or nitrogen donor systems such as carboxylic acids, 1,3-diketonates, hydroxy carboxylic acids, Schiff bases including acyl phenols and iminoacyl groups. As is known, luminescent lanthanide metal complexes require sensitizing group(s) which have the triplet excited energy level higher than the first excited state of the metal ion.

A wide range of luminescent low molecular weight metal complexes are known and have been demonstrated in organic light emitting devices [see, e.g., Macromol. Sym. 125 (1997) 1-48, U.S. Pat. No. 5,150,006, U.S. Pat. No. 6,083,634 and U.S. Pat. No. 5,432,014]. Suitable ligands for di or trivalent metals include oxinoids (e.g. with oxygen-nitrogen or oxygen-oxygen donating atoms, generally a ring nitrogen atom with a substituent oxygen atom, or a substituent nitrogen atom or oxygen atom with a substituent oxygen atom such as 8-hydroxyquinolate and hydroxyquinoxalinol), 10-hydroxybenzo(h)quinolinato, benzazoles, schiff bases, azoindoles, chromone derivatives, 3-hydroxyflavone, and carboxylic acids such as salicylato (VIII) amino carboxylates and ester carboxylates.

The d-block metals form organometallic complexes with carbon or nitrogen donors such as porphyrin, 2-phenyl-pyridine, 2-thienylpyridine, benzo(h)quinoline, 2-phenylbenzoxazole, 2-phenylbenzothiazole or 2-pyridylthianaphthene and iminobenzenes. The (hetero)aromatic rings in these groups can be substituted.

When m is zero there is no DENDRON group attached to group $-[X]_r$. When m is one, then a DENDRON group is present. The subscripts m need not be the same in any one compound, however preferably all subscripts m are either zero or one. Similarly, when r is zero there is no -[X]- group between the CORE and the DENDRON. As is made clear above, it is necessary that, for every point of attachment, at least one of m and r is greater than zero. Whether X groups or DENDRON groups are present can be decided in order to tailor the properties of the compounds. In the case of organometallic COREs, it is preferable that X groups are not present. X groups have a tendency to quench the phosphorescence of phosphorescent organometallic COREs and are hence less preferred. However, in the case of fluorescent organometallic or organic COREs, X groups may be preferred.

The $-[X]_r-$ group, preferably represents chains of aryl, heteroaryl, iptycene, vinyl and/or acetylene groups and/or metal complexes or derivatives thereof. These groups are joined in series, rather than forming branched structures. Preferably each $-[X]_r-$ group comprises at least three aryl, heteroaryl and/or iptycene groups joined in series and optionally linked via acetylene and/or vinylene groups. Preferred aryl and heteroaryl groups include phenyl, naphthyl, anthracenyl, fluorenyl, thiophene and pyridine, for example phenyl, naphthyl, fluorenyl, thiophene and pyridine, with phenyl and fluorenyl being most preferred. The aryl and/or heteroaryl groups in X need not be identical. For example, suitable X groups include a phenyl-fluorenyl-fluorenyl group.

When m is zero and $-[X]_r$ is a terminal group, it preferably comprises from 1 to 10 groups in series. Where vinylene and/or acetylene groups are present, they are preferably disposed between aryl and/or heteroaryl groups.

In one embodiment r is an integer of from 2 to 10, more preferably from 2 to 5, more preferably 2 or 3, for example 3, and each X is the same or different and represents a monocyclic aryl or heteroaryl group. In another embodiment r is an integer of from 1 to 10, more preferably from 1 to 5, more preferably 1 or 2, for example 1, and each X is the same or different and represents a polycyclic aryl or heteroaryl group, for examples it is a bi-, tri- or higher-cyclic group.

In a preferred embodiment, when m is zero and r is one, the X group present is a polycyclic aryl or heteroaryl group. Thus, when $-[X]_r$ is a terminal group which comprises only one aryl or heteroaryl group, it is preferably a relatively large group. For example, it is preferably a bi-, tri- or higher-cyclic group, preferably a tri- or higher-cyclic group, more preferably a group having more than three rings. Suitable groups include porphyrin, pyrene and perylene and other such polycyclic groups.

In another preferred embodiment, when m is zero and r is greater than one, the X groups present represent aryl and/or heteroaryl groups and/or planar metal complexes and/or vinylene or acetylene groups. Preferred aryl and/or heteroaryl groups include any monocyclic or higher groups, including those listed above when m is zero and r is one. More preferred groups include mono-, bi and tricyclic groups, for example phenyl and fluorenyl. The X groups in this embodiment are the same or different. Furthermore, preferably when vinylene or acetylene groups are present they are located between other X groups (e.g. phenyl and fluorenyl), rather than being at the extremities of the $-[X]_r$ group. In this embodiment r is preferably from 2 to 6, more preferably from 2 to 4, for example 2 or 3.

When m is one and DENDRON is hence present, and when r is one, then $-[X]_r-$ is preferably as defined above in relation to embodiments where m is zero and r is one. Thus when $-[X]_r-$ is a single group it is preferably a larger group, e.g. a bi-, tri- or higher-cyclic aryl or heteroaryl group. In contrast, when r is greater than one and there are hence more than one X groups present, preferred X groups are generally smaller groups, for example phenyl and fluorenyl.

When X comprises an iptycene or derivative thereof, preferred iptycenes include triptycene and pentiptycene, with triptycene being preferred. The iptycene can be unsubstituted or substituted. If substituents are included, suitable substituents include those discussed as substituents in US patent application 2005/0196775.

The X groups are unsubstituted or substituted. Suitable substituents will be determined taking into account the desired solubility and also taking into account steric and electronic factors. For example, any substituents on the X groups should be chosen to avoid an unfavourable reduction in the interactions between target analyte and chromophore, whether that is by physically blocking any interaction between the chromophore and target analyte, or by reducing or otherwise unfavourably altering the electronic interaction between chromophore and target analyte. When substituents are present, preferred examples include $C_{1-6}$ alkyl, $C_{1-6}$ alkoxy, hydroxy($C_{1-4}$ alkyl), hydroxyhalo($C_{1-4}$)alkyl and hydroxy, for example fluorinated alcohols, and the like, with alkyl groups such as $C_{1-4}$ alkyl groups being preferred. These substituents may be chosen to aid in the detection of the target analyte, for example in the detection of explosives. The skilled person will be able to determine preferred substituents and substituent combinations depending on the target analyte to be detected.

In exemplary compounds, X comprises at least one phenyl group, and the phenyl group or groups are preferably unsubstituted. When X comprises at least one fluorenyl group, preferred substituents include $C_{1-4}$ alkyl groups, for example one or two propyl groups.

When $-[X]_r-$ comprises a metal complex, the metal complex is preferably present at the end of the $-[X]_r-$ groups which is distant from the CORE, i.e. either the termination of the molecule or the portion of $-[X]_r-$ bonded to DENDRON.

DENDRON, where present, is the same or different and represents an at least partially conjugated dendritic molecular structure comprising at least one branching group and optionally at least one linking group, the branching groups being selected from aryl and heteroaryl groups and nitrogen atoms, and the linking groups being selected from aryl, heteroaryl, vinyl and acetylenyl groups, said branching groups being bonded to three or more groups, and said linking groups being bonded to two groups, said dendritic molecular structure terminating at its distal points in aryl and/or heteroaryl groups.

The branching groups in DENDRON are selected from aryl and heteroaryl groups and nitrogen atoms because these groups are at least trivalent and are hence capable of bonding to three or more groups. One of said groups to which a branching group is bonded will be a branching or linking group of the previous generation, or the X group or CORE to which DENDRON is bonded. The other two or more groups will be linking groups and/or branching groups of the next generation, or the aryl and/or heteroaryl groups which terminate the dendritic molecular structure. In the case of nitrogen, which is capable of bonding to up to four groups, when it is a branching group it will preferably bond to three groups only.

When a branching group is an aryl group, suitable groups include phenyl, naphthalene, anthracene and, where appropriate, substituted variations. Preferably, when a branching group is an aryl group it is a phenyl ring. More preferably the branching group is a phenyl ring coupled at ring positions 1, 3 and 5. When a branching group is a heteroaryl group, suitable groups include pyridine, carbazolyl, triazole, triazine and, where appropriate, substituted variations. Carbazolyl is preferred.

The branching groups are unsubstituted or substituted, but are preferably unsubstituted (other than bonding to the X or CORE groups or to other branching or linking groups or the groups which terminate the dendritic molecular structure).

The linking groups in DENDRON are selected from aryl, heteroaryl, vinyl and acetylenyl groups. The linking groups are chosen because they are able to form divalent moieties, which are capable of bonding to two groups. The groups to which said linking groups are bonded include other linking groups, branching groups and/or the aryl and/or heteroaryl groups which terminate the dendritic molecular structure.

When a linking group is an aryl group, suitable groups include $C_{6-14}$ aryl groups such as phenyl, naphthalenyl, anthracenyl, fluorenyl and, where appropriate, substituted variations. Preferably, when a linking group is an aryl group it is a phenyl or fluorenyl group. When the linking group is a phenyl ring, it is preferably coupled at ring positions 1 and 4. When the linking group is a fluorenyl ring, it is preferably coupled at ring positions 2 and 7.

The linking groups are unsubstituted or substituted. When a linking group is aryl, it is preferably an unsubstituted phenyl, or a fluorenyl which is unsubstituted or substituted by 1 or 2 groups at the 9-position. Preferably when a linking group is aryl it is unsubstituted phenyl or unsubstituted or substituted fluorenyl.

More than one of the moieties described as linking groups above can couple together to form larger linking groups. For example, a phenyl ring and a further phenyl ring can couple to form a biphenyl group which can itself be a linking group between two branching groups or between a branching group and an aryl or heteroaryl ring which terminates the dendritic molecular structure.

The dendritic molecular structure terminates at its distal points in aryl and/or heteroaryl groups. Preferred such aryl and/or heteroaryl groups include phenyl groups.

The compounds of formula (I) of the invention may comprise one or more substituents, particularly on the X groups or DENDRON groups, and more particularly on the DENDRON groups. Generally the substituents are chosen such that the dendrimers have increased solubility in the solvent in which they will be processed. Such groups are therefore termed "solubilising groups". When the solubilising groups are attached to the distal aryl or heteroaryl groups or the dendrons they are termed "surface groups". In particular, preferred surface groups are those which are capable of improving the solubility of the claimed dendrimers in solvents suitable for solution processing. Accordingly, suitable surface groups include those which result in the dendrimers having increased solubility in solvents such as tetrahydrofuran, toluene, chloroform, chlorobenzene, xylenes and alcoholic solvents such as methanol.

The surface groups are capable of changing the electronic properties of the moieties to which they are attached. The groups preferably impart good solubility to the dendrimers and may also contain moieties that allow patterning and/or cross-linking. The attachment position and number of the surface groups attached to the aryl and heteroaryl moieties is dependent on their structure and well known to those skilled in the art of organic chemistry. Suitable surface groups include those disclosed in PCT/GB02/00750, to which reference should be made for further details. Suitable surface groups include hydroxy, $C_{1-15}$ alkyl, $C_{2-15}$ alkenyl, amine, $C_{1-15}$ alkylamine, di($C_{1-15}$)alkylamine, —COOR wherein R is hydrogen or $C_{1-15}$ alkyl, $C_{1-15}$ is alkoxy, $C_{2-15}$ alkenyloxy, $C_{6-10}$ aryloxy, —$O_2$SR wherein R is $C_{1-15}$ alkyl or $C_{2-15}$ alkenyl, —$SiR_3$ wherein each R is the same or different and represents hydrogen, $C_{1-15}$ alkyl or $C_{2-15}$ alkenyl, $C_{1-15}$ alkylthio, $C_{2-15}$ alkenylthio, $C_{6-10}$ arylthio, $C_{6-14}$ aryl and 5- to 10-membered heteroaryl, wherein the groups $C_{6-10}$ aryl and 5- to 10-membered heteroaryl, when present, are substituted with from one to five substituents which are themselves unsubstituted and are selected from $C_{1-15}$ alkyl, $C_{2-15}$ alkenyl, $C_{1-15}$ alkoxy and $C_{2-15}$ alkenyloxy.

Particularly preferred surface groups include $C_{1-15}$ alkyl, $C_{1-15}$ alkoxy, and substituted $C_{6-14}$ aryl groups where the substituents are selected from $C_{1-15}$ alkyl and $C_{1-15}$ alkoxy. When the surface groups are selected from substituted $C_{6-14}$ aryl groups, preferred aryl groups include phenyl and fluorenyl, more particularly substituted fluorenyl. Preferred substituents on the $C_{6-14}$ aryl groups include $C_{1-15}$ alkyl groups and $C_{1-15}$ alkoxy groups, particularly $C_{1-10}$ alkyl and $C_{1-10}$ alkoxy groups. For example, n-propyl, t-butyl, methoxy and ethoxy surface groups may be used as substituents on the $C_{6-14}$ aryl group, or straight or branched chain $C_8$ alkoxy groups such as 2-ethylhexyloxy. Preferably the substituents are selected from $C_{1-10}$ alkyl groups. Preferably the $C_{6-14}$ aryl group carries from one to four substituents, more preferably from one to three substituents, most preferably one or two substituents.

When the surface groups are selected from $C_{1-15}$ alkyl groups, $C_{1-10}$ alkyl groups are preferred, such as methyl and ethyl, and straight or branched chain propyl and butyl. For example, surface groups include n-propyl and t-butyl. When the surface groups are selected from $C_{1-15}$ alkoxy groups, $C_{1-10}$ alkoxy groups are preferred, for example 2-ethylhexyloxy.

Different surface groups may be present on different dendrons or different distal groups of a dendron. Where t-butyl groups are the surface groups attached to phenyl rings it is preferable that more than one is attached to each of the distal phenyl units.

The surface groups can also be chosen such that the dendrimer can be patterned. For example, a crosslinkable group can be chosen, which can be crosslinked upon irradiation or by chemical reaction. Alternatively, the surface groups can comprise protecting groups that can be removed to leave crosslinkable groups. Accordingly, the dendrimers of the invention may also comprise one or more reactable groups which can be reacted in order to cross-link. Suitable cross-linking groups include oxetanes.

The surface groups can also be chosen to bind to a specific substrate. For example, thiols could be used to bond the materials to gold film.

The aryl and/or heteroaryl groups which terminate the molecule may have a number of substituents, for example substituents described as surface groups above. However, preferred substituents include $C_{1-10}$ alkyl groups and $C_{1-10}$ alkoxy groups, for example $C_8$ alkoxy groups like 2-ethylhexyloxy.

Compounds of Formula (II):

The $-[X]_r-$ group in formula (II) is a linker group between the two or more DENDRON or DENDRON$^1$ groups and provides at least (p+q) points of attachment, each point of attachment being bonded to a DENDRON or DENDRON, group. Preferably each point of attachment is on a different X group. More preferably, the terminal X groups (e.g. in a chain $-X_1-X_2-X_3-X_4-$ it would be the $-X_1-$ and $-X_4-$ groups) bear the DENDRON or DENDRON$^1$ groups. In this scenario, it is preferred that p is zero and q is two.

As with formula (I), the subscript p is preferably zero, one or two. The subscript q is preferably from 1 to 6, more preferably from 2 to 6, more preferably from 2 to 4, for example 2. Accordingly, there are preferably 2 DENDRON groups attached to the $-[X]_r-$ group.

In the case of compounds of formula (II), it is possible for r to be zero, but more preferably r is an integer of from 1 to 10. When r is one, the X group present is preferably a relatively large group, for example a bi-, tri- or higher-cyclic aryl or heteroaryl group, such as those discussed earlier in relation to formula (I).

When r is greater than 1, then the X groups present need not be so large. The preferred X groups in this embodiment are the same as the preferred X groups for compounds of formula (I) where r is greater than one. Thus, most preferred groups are aryl and/or heteroaryl groups, in particular phenyl and fluorenyl. Also, when at least one X group is vinylene or acetylene groups, these are preferably between the aryl and/or heteroaryl groups of the X group. When the vinylene and/or acetylene groups are present at the distal end of X, they are preferably bonded to the first branching group of DENDRON. When r is greater than one, X may be the same or different.

The X groups in $-[X]_r-$ are unsubstituted or substituted, with suitable substituents including $C_{1-8}$ alkyl groups such as $C_6$ alkyl groups. For example, when the $-[X]_r-$ comprises at least one fluorenyl group, this can be substituted by hexyl groups, for example by two hexyl groups. The substituents can be manipulated in order to achieve the desired response to the target analyte to be tested. Other suitable substituents include hydroxy($C_{1-4}$)alkyl and hydroxyhalo($C_{1-4}$)alkyl groups, for example fluorinated alcohols.

Where an X group is a planar metal complex, said complex comprises a central metal atom surrounded by ligands, with the ligands bearing the DENDRON and optional DENDRON$^1$ groups. The complex is preferably coordinated by ligands bearing the DENDRON and optional DENDRON$^1$ groups in a linear, trigonal planar or square planar configuration. With regard to linear complexes, the metals in such complexes are coordinated to two ligands bearing two DENDRON groups or one DENDRON group and one DENDRON$^1$ group in a linear orientation. Additional co-ligands may also be present in such complexes. Suitable metals in such complexes are therefore metals which tend to form planar complexes, and in particular zinc, platinum and palladium.

The preferred DENDRON groups are as defined earlier in relation to the compounds of formula (I). Similarly, the preferred DENDRON$^1$ groups are also as defined earlier in relation to the compounds of formula (I).

Testing:

The compounds of the invention have been tested with dinitrobenzene in order to determine their ability to detect similar compounds. The photoluminescence spectra were recorded both before exposure to dinitrobenzene, and at a number of intervals after exposure. The findings show that dinitrobenzene causes a noticeable quenching of the luminescence. Thus after exposure to dinitrobenzene in the test substance the photoluminescence is reduced, but this can be recovered by removal of the dinitrobenzene. This latter step can be achieved, for example, by exposing to an inert gas flow, e.g. placing the substance under a flow of nitrogen. Some time after removal of the dinitrobenzene, the photoluminescence does in fact return to near its original, pre-exposure level, indicating that the compounds could be recycled and used for further detection experiments.

In some embodiments, as shown above, the ability of the sensor to sense the presence of a target analyte will be reversible, with the sensor being regenerated by removing the target analyte and exposing the sensor to a substance with which the chromophores do not interact and which will hence return the luminescence of the compound of formula (I) or (II) to its original state. This is preferred.

However, in some embodiments the ability of the sensor may not be reversible. For example, the target analyte may formally react with the compound of formula (I) or (II) in such a way that it cannot be removed. In such a scenario, the sensor will not be capable of being regenerated. This could be the case when the sensor is used to sense the nerve agents discussed previously, for example sarin, VX and soman.

Processes:

The materials can be made in either a convergent or divergent method or a combination of both. In some circumstances a convergent route may be preferred. For example, for compounds of formula (I) where the CORE is a metal complex, the DENDRON$^1$ group and $-[X]_r-[DENDRON]_m$ groups can be attached to the appropriate ligands and these are subsequently attached to the metal ion. Optionally where the synthetic route allows, other ligands without DENDRON or DENDRON$^1$ groups can subsequently be attached to said complex. Alternatively a ligand with a suitably reactive functional group can be complexed to the metal ion, and then reacted with appropriately functionalised dendrons. In this latter method, not all ligands have to have the reactive functional groups, and thus this method allows the attachment of dendrons to some but not all of the ligands complexed to the metal.

In other circumstances, for example where the CORE for formula (I) is organic, it may be preferred to prepare the materials using a divergent method. For example, the CORE may be provided with suitable functional groups already attached or with X groups already attached, and this may then be further reacted with suitable reagents in order to extend the X group or to add constituents of the DENDRON or DENDRON, groups. For compounds of formula (II), it is generally preferred to use a convergent strategy.

Devices:

The sensors of the present invention can be designed in a number of ways, but in all cases comprise a compound of formula (I) or formula (II) as defined earlier. For example, the sensor may comprise a single region of such a compound, along with an excitation source and detector capable of measuring the electronic and/or optical properties (e.g. the luminescence) of the compound. By comparing the measurements both before and after exposure to the analyte, it can be determined whether the electronic and/or optical properties have changed.

Suitable excitation sources include lasers and light emitting diodes (LEDs), particularly those from gallium nitride. Suitable detectors include photodiodes. Wavelength selection could be supplied by bandpass or interference filters, or alternatively a monochromator. In one particular embodiment an organic light emitting diode (OLED) can be used as the excitation source with an organic photodiode as the detector.

In a preferred embodiment, the compound, which is preferably in the solid state, will first be excited and caused to luminesce, with the luminescent properties (e.g. the quantum yield or wavelength of the luminescence) being measured. The compound will then be exposed to the test substance which may or may not contain the target analyte which is to be detected. During or after exposure, the compound will again be excited and caused to luminescence, with the luminescent properties again being measured. The two sets of luminescent properties can then be compared. If there is a change in luminescent properties, this is indicative of the presence of a target analyte which has bound to or become associated with the compound. For example, the target analyte may cause quenching of the luminescence which can be detected. If the luminescence of the compound is quenched following exposure to the target analyte, this will therefore indicate that the target analyte is present in the test substance. Other suitable sensor structures are known, for example those used in WO-A-99/57222. In other embodiments, the sensor could be a field effect transistor (FET).

In another preferred embodiment, a sensor comprises a first region of a compound of formula (I) or (II), encapsulated to give a reference luminescence (e.g. a reference fluorescence). The sensor further comprises a second region of the same compound, which is not encapsulated and which can therefore interact with the surrounding atmosphere. By comparing the luminescent properties of the first and second regions, presence of the target analyte in the atmosphere can be determined. An alternative approach would be to provide a first region of a compound of formula (I) or (II) and a second region of a different compound, the different compound having luminescent properties which are not altered in the presence of the target analyte to be sensed or for which the luminescent properties change in a different way from the change observed in the compound of formula (I) or (II) following exposure to the target analyte. By exposing both regions to the substance to be tested and comparing the luminescent properties observed, presence of the target analyte can be determined.

A sensor according to the invention may also comprise more than one compound of formula (I) or formula (II). The compounds may be chosen to be sensitive towards different target analytes. By measuring the response of each compound, different target analytes may be detected using the same sensor.

The sensors preferably employ the compounds of formula (I) or formula (II) in the form of a thin film, and the properties of compounds allow them to be solution processed and deposited in the form of a film. The compounds can be dissolved in a solvent, the solution deposited onto a substrate, and the solvent removed to leave a solid film. Conventional solution-processing techniques can be used, for example spin-coating, printing (e.g. ink-jet printing) and dip-coating. A solid film containing the compounds is preferably either fluorescent or phosphorescent. The solid film is preferably formed on one side of a substrate and the thickness of the solid film is preferably less than 2 microns, for example up to about 150 nm. In fact, the target analyte molecules may not diffuse far into the films, and it may therefore be preferred to use relatively thin films, for example from 10 to 150 nm, more preferably from 10 to 100 nm. While higher film thicknesses can be used, it has been found that thicker films result in a lower quenching response and hence a lower sensitivity.

In one embodiment, a film of the compounds used in the invention may consist essentially of said compound. Small amounts of other substances may be present in such layers, for example impurities or additives which improve the film-forming properties of the compound. However, in this embodiment these other substances are preferably present in a small amount, for example less than about 5 wt %, more preferably less than about 3 wt %, for example less than about 1 wt %. In particular, it is preferred that if any small amounts of other substances are present, these are merely present as a separate component in the film, and are not chemically linked (e.g. covalently linked) to the compounds of formula (I) or (II). Most preferably the films used in the invention are essentially neat films of the compound of formula (I) or formula (II).

In another embodiment, the compound used in the invention is blended with another material and is present at a lower level, such as at a level of from 10 to about 80 wt %, more preferably from 10 to about 50 wt %, such as around 20 wt %. The other material present in the blend may be one or more other dendrimers and/or polymers and/or molecular materials. Preferably the other material present in the blend is not a metallic or semiconductor nanoparticle, for example a gold nanoparticle. Again, it is preferred that the other materials present in the blends, in addition to the compounds of formula (I) or (II), are present as separate components which are not chemically linked (e.g. covalently linked) to the compounds of formula (I) or (II).

The films can be patterned using conventional methods including photopatterning, deposition on a patterned substrate (non-planar substrate) or by soft-lithography. Patterning of the material by deposition on a non-planar substrate or soft-lithography would increase the surface area of the film and if the pattern in the film is of the correct wavelength scale it can lead to films that lase. If the film lases then there can be increased sensitivity to the interaction with a target analyte. Patterning of dendrimer films for lasing is envisaged. Where the patterning allows the deposition of different compounds of the invention, for example photopatterning or inkjet printing, different target analytes could be sensed in the same device.

The invention will be described in the Examples which follow.

EXAMPLES

Measurements and Materials

For this study, dendrimers of different dimensionality and electron affinity containing the same bisfluorene units were compared.

Example 1

Synthesis of Compound 1

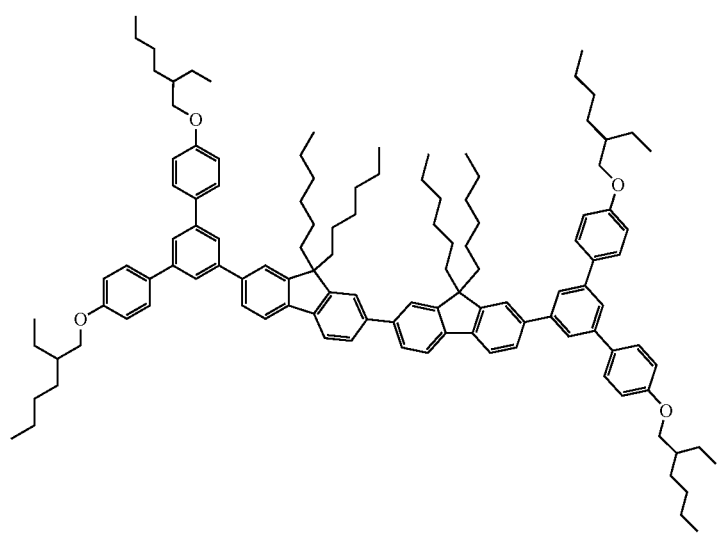

A mixture of 3,5-bis(4-ethylhexyloxyphenyl)phenylboronic acid (796 mg, 1.5 mmol), 2-bromo-7-(2-bromo-9,9-dihexyl-9H-fluoren-7-yl)-9,9-dihexyl-9H-fluorene (412 mg, 0.5 mmol), tetrakis(triphenylphosphine)palladium(0) (87 mg, 0.075 mmol), and sodium carbonate (64 mg, 106 mmol) in a round bottom flask was degassed with argon. Toluene (1 mL), water (300 µL), and ethanol (300 µL) were added, and the flask was degassed and purged with argon before heating at reflux for 24 h. After cooling, toluene (10 mL) and water (10 mL) were added, and the layers were separated, dried over anhydrous magnesium sulfate, filtered, and solvent removed. The residue was purified by column chromatography over silica using a light petroleum:dichloromethane mixture (1:0-91:9) as eluent to give 1 (635 mg, 78%). (400 MHz; $CDCl_3$) 0.7-1.0 (50H), 1.1-1.5 (50H), 1.72 (4H, 2.1 (8H), 3.9 (8H), 7.0 (8H), 7.4-7.8 (26H). (MALDI:dithranol) 1635.36, exact mass 1635.18.

Example 2

Synthesis of 3,6-bis(4-(2-ethylhexyloxy)phenyl)-9-(2-(2-(3,6-bis(4-(2-ethylhexyloxy)phenyl)-9H-carbazol-9-yl)-9,9-dihexyl-9H-fluoren-7-yl)-9,9-dihexyl-9H-fluoren-7-yl)-9H-carbazole (2)

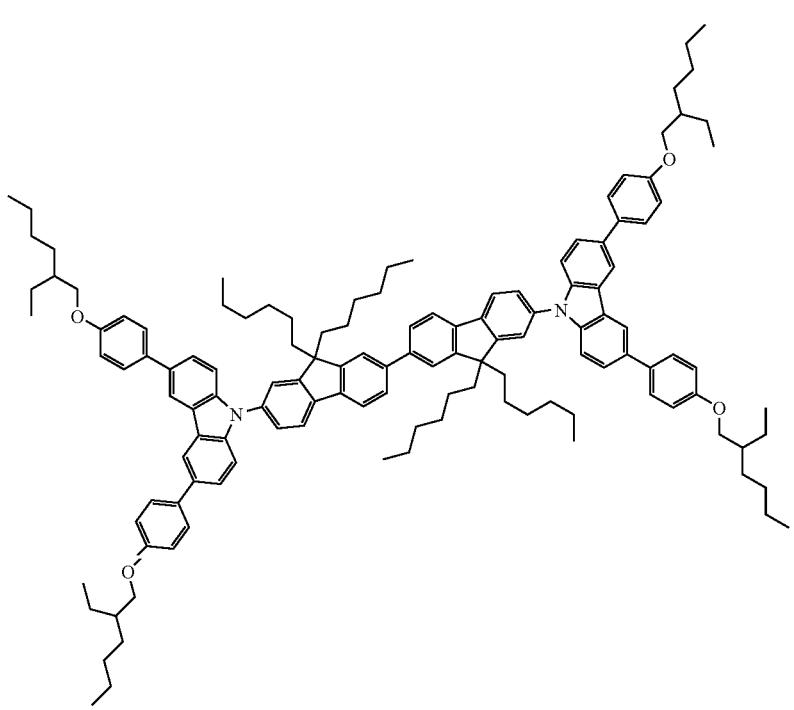

A mixture of 3,6-bis(4-(2-ethylhexyloxy)phenyl)-9H-carbazole (S.-C. Lo et al, Organic Electronics, in press) (882 mg, 1.46 mmol), 2-bromo-7-(2-bromo-9,9-dihexyl-9H-fluoren-7-yl)-9,9-dihexyl-9H-fluorene (412 mg, 0.5 mmol), palladium(0) dibenzylidineacetone (23 mg, 0.025 mmol), and sodium t-butoxide (144 mg, 1.5 mmol) was degassed and purged with argon, before a 10% solution of tri-tert-butyl phosphine in hexane (202 μL, 0.1 mmol) was added. Toluene (1 mL) was added and the mixture was heated to 130° C. for 84 h. The cooled solution and toluene (20 mL) was added. The organic layer was washed with water (15 mL) and brine (15 mL), dried over anhydrous magnesium sulfate, filtered, and the solvent removed. The residue was purified using by column chromatography over silica using a light-petroleum/toluene mixture (1:4) as eluent to give 2 (373 mg, 41%). (400 MHz; CDCl$_3$) 0.75-1.0 (70H), 1.3-1.6 (30H), 1.78 (4H), 2.1 (8H), 3.9 (8H), 7.04 (8H), 7.52 (4H), 7.55-7.75 (18H) 7.75 (2H), 7.89 (2H), 7.98 (2H), 8.38 (4H). (MALDI:dithranol) 1812.63, exact mass 1813.24.

Example 3

Synthesis of 1,3,5,7-tetrakis(4-(2-(9,9-dipropyl)-fluorenyl)phenyl)adamantane (3a)

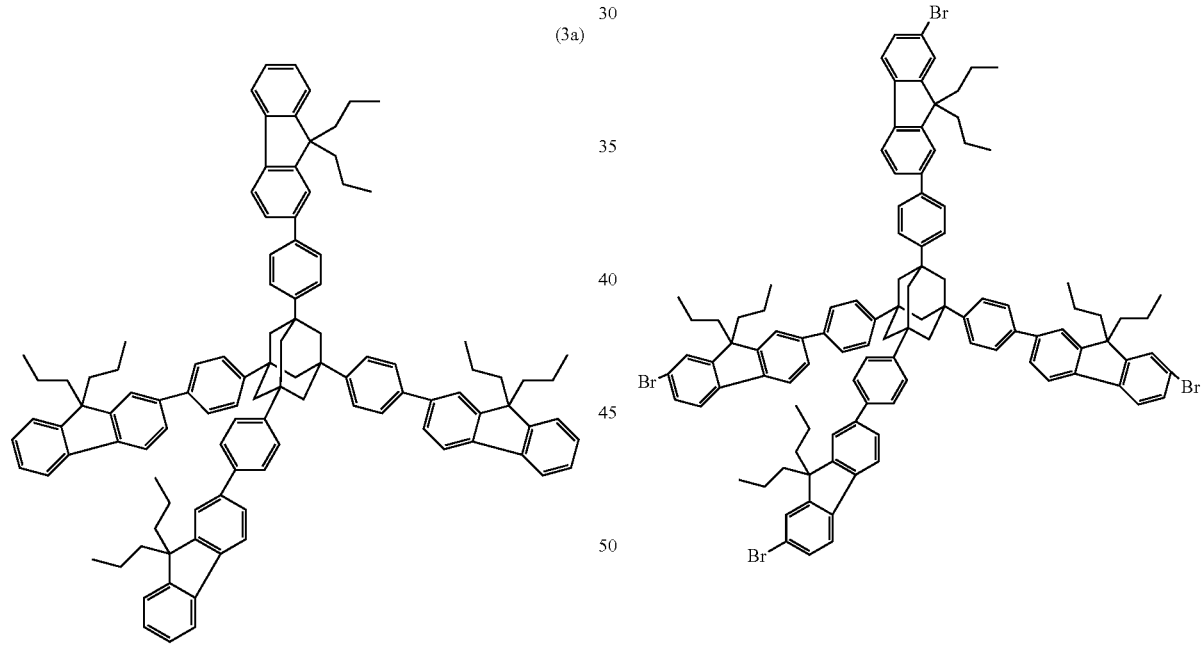

A mixture of 1,3,5,7-Tetrakis(−4-iodophenyl)adamantane (1.36 g, 1.434 mmol), 9,9-dipropylfluorene-2-boronic acid (2.109 g, 7.17 mmol) and tetrakis(triphenylphosphine)palladium(0) (166 mg, 0.143 mmol) was flushed with argon. Toluene (7 cm$^3$) was then added and the reaction mixture was stirred whilst being degassed and purged with argon 4 times. Aqueous sodium carbonate (4 cm$^3$, 2 M) and degassed ethanol (4 cm$^3$) were added after which, the reaction mixture was stirred at reflux for 72 h. The reaction mixture was then cooled to room temperature and hydrogen peroxide (3 cm$^3$, 30% w/w) was added and stirred for 1 hr. Toluene (30 cm$^3$) was then added and the layers were separated. The aqueous layer was extracted with toluene (2×30 cm$^3$). The combined organic extracts were washed with brine (30 cm$^3$), dried over anhydrous magnesium sulfate and filtered. The solvent was removed to give a brown solid, which was purified by column chromatography over silica using a light petroleum/dichloromethane mixture (10:2 to 0:10) as eluent. The solid produced was further purified by recrystallisation using an ethyl acetate/methanol mixture to yield 3a (1.13 g, 64%), mp 246-250° C.; (Found; C, 92.11; H, 7.79. C$_{110}$H$_{112}$ requires; C, 92.13; H, 7.87%); δ$_H$ (400 MHz; CDCl$_3$) 0.58-0.82 (40H), 1.90-2.08 (16H), 2.29-2.43 (12H), 7.28-7.42 (12H), 7.53-7.81 (32H).

Example 4

Synthesis of 1,3,5,7-tetrakis(4-(2-(7-bromo-(9,9-dipropyl)-fluorenyl))phenyl)adamantane (3b)

3a (1.00 g, 0.69 mmol) was dissolved in dichloromethane (10 cm$^3$) and bromine (142 μl, 2.792 mmol) was added to the solution. The reaction was stirred at reflux for 1 hr before cooling back to room temperature. Methanol was added to form a precipitate which was then collected by filtration, washed with methanol and purified by re-precipitation using a dichloromethane/methanol mixture to give 3b (1.08 g, 95%), mp 216-221° C.; (Found; C, 75.67; H, 6.15. C$_{110}$H$_{108}$Br$_4$ requires; C, 75.51; H, 6.22%); δ$_H$ (400 MHz; CDCl$_3$) 0.62-0.85 (40H), 1.80-2.15 (16H), 2.22-2.50 (12H), 7.32-7.52 (9H), 7.53-7.44 (12H), 7.45-7.85 (19H).

Example 5

Synthesis of 1,3,5,7-tetrakis(4-(7-(2'-(9',9'-dipropyl)fluorenyl)-(2-(9,9-dipropyl)fluorenyl)phenyl)adamantane (3)

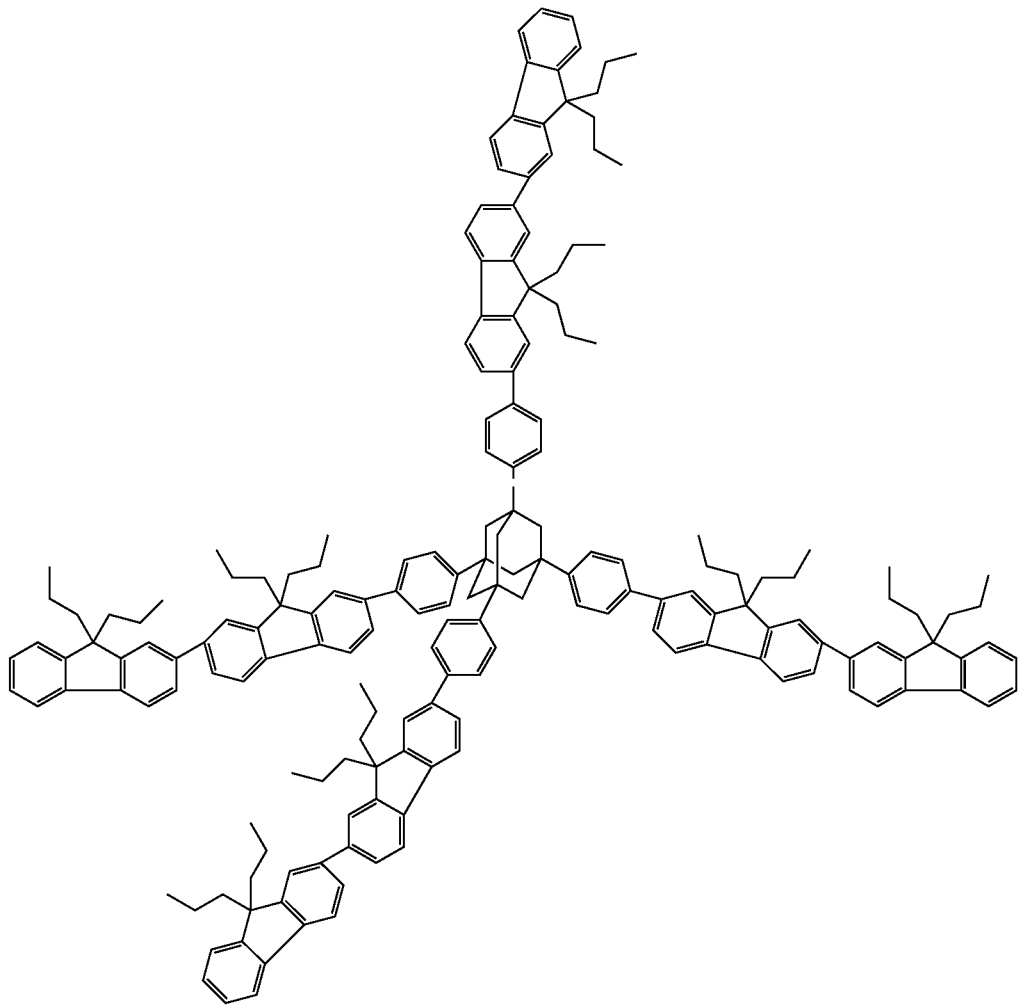

3

3b (870 mg, 0.497 mmol) and 9,9-dipropylfluorene-2-boronic acid (731.4 mg, 2.49 mmol) and tetrakis(triphenylphosphine)palladium(0) (101 mg, 0.094 mmol) were added to a round bottom flask and flushed with argon. Toluene (3 cm$^3$) was added and the mixture was degassed and purged with argon three times. Aqueous sodium carbonate (1.25 cm$^3$, 2 M) and degassed ethanol (1.25 cm$^3$) were added after which, the reaction mixture was then stirred at reflux for 44 hrs. The reaction mixture was cooled to room temperature and hydrogen peroxide (2.5 cm$^3$, 30% w/w) was added. The reaction mixture was stirred for 1 hr. Toluene (20 cm$^3$) was added and the layers separated. The aqueous layer was extracted with toluene (2×20 cm$^3$), and the combined organic extracts were washed with brine (20 cm$^3$), dried over magnesium sulfate, and filtered. The solvent was completely removed in vacuo to give a brown solid. The residue was then purified by column chromatography over silica using a light petroleum/dichloromethane mixture (10:0 to 10:2) as eluent. This gave a white solid, which was then purified further by precipitation from a dichloromethane/methanol mixture to give 3. (0.774 g, 64%), mp 234-238° C.; (Found; C, 92.03; H, 7.92. $C_{186}H_{192}$ requires; C, 92.03; H, 7.97%); $\delta_H$ (400 MHz; CDCl$_3$) 0.45-1.05 (80H), 1.82-2.18 (32H), 2.20-2.69 (12H), 7.29-7.5 (18H), 7.51-8.00 (50H).

Example 6

Synthesis of 1,3,5,7-tetrakis(4-(7-(2'-(7'-bromo-(9', 9'-dipropyl)fluorenyl))-(2-(9,9-dipropyl)fluorenyl) phenyl)adamantane (4a)

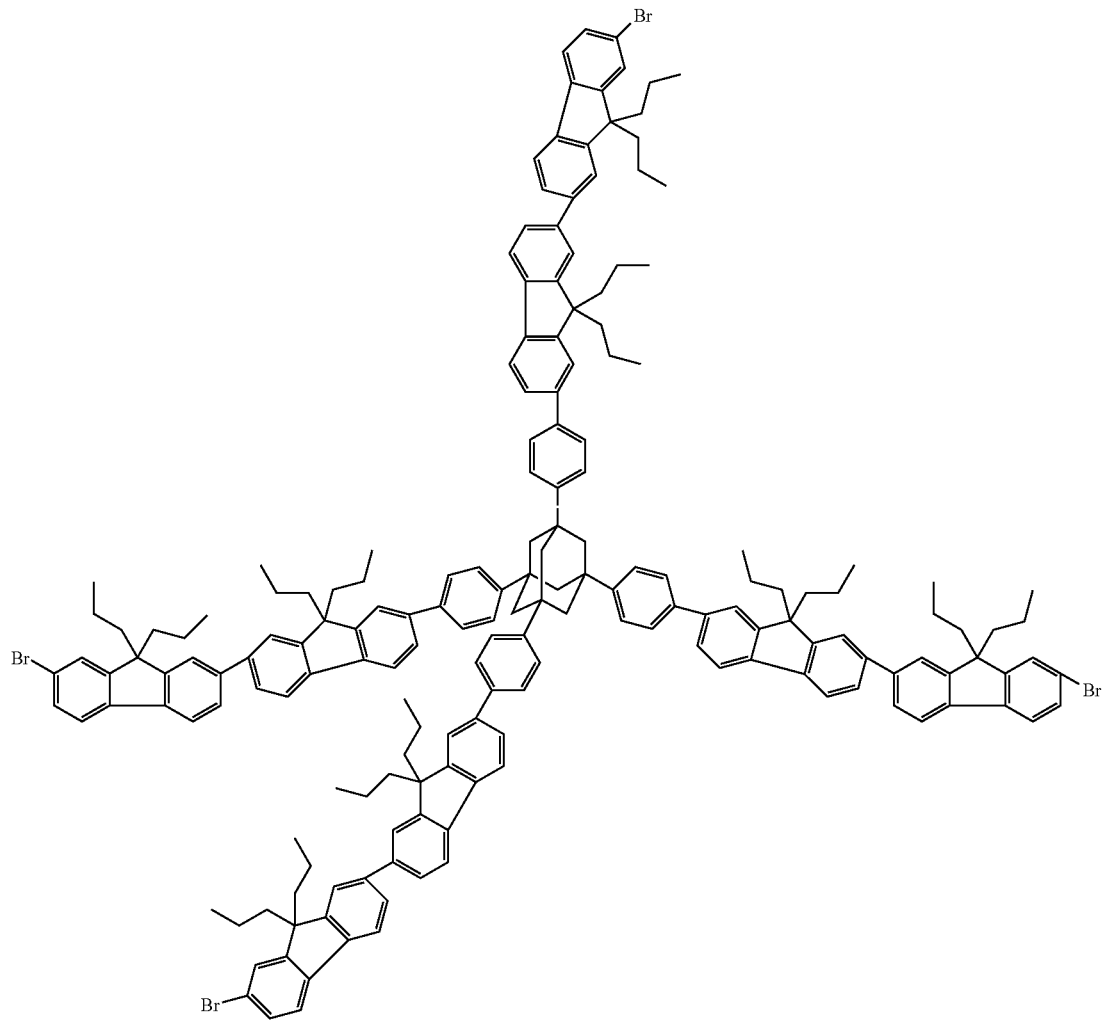

3 (500 mg, 0.824 mmol) was dissolved in dichloromethane (5 cm$^3$). Bromine (42 μl, 0.824 mmol) was then added and the reaction mixture was stirred at reflux for 1 hr before cooling to room temperature. Methanol was added until a precipitate was formed which was isolated by filtration, washed with methanol, and then purified by re-precipitation using a dichloromethane/methanol mixture to give 4a (0.5413 g, 96%), Mp 256-260° C.; (Found; C, 69.16; H, 5.58. $C_{186}H_{188}Br_4$ requires; C, 81.44; H, 6.91%); δ$_H$ (400 MHz; CDCl$_3$) 0.55-0.95 (80H), 1.75-2.15 (32H), 2.25-2.55 (12H), 7.30-8.20 (64H).

Example 7

Synthesis of 1,3,5,7-tetrakis(4-(7-(2'-(7'-(3,5-di(4-(2-ethylhexyloxy)phenyl)phenyl)-(9',9'-dipropyl)fluorenyl))-(2-(9,9-dipropyl)fluorenyl)phenyl)adamantane (4)

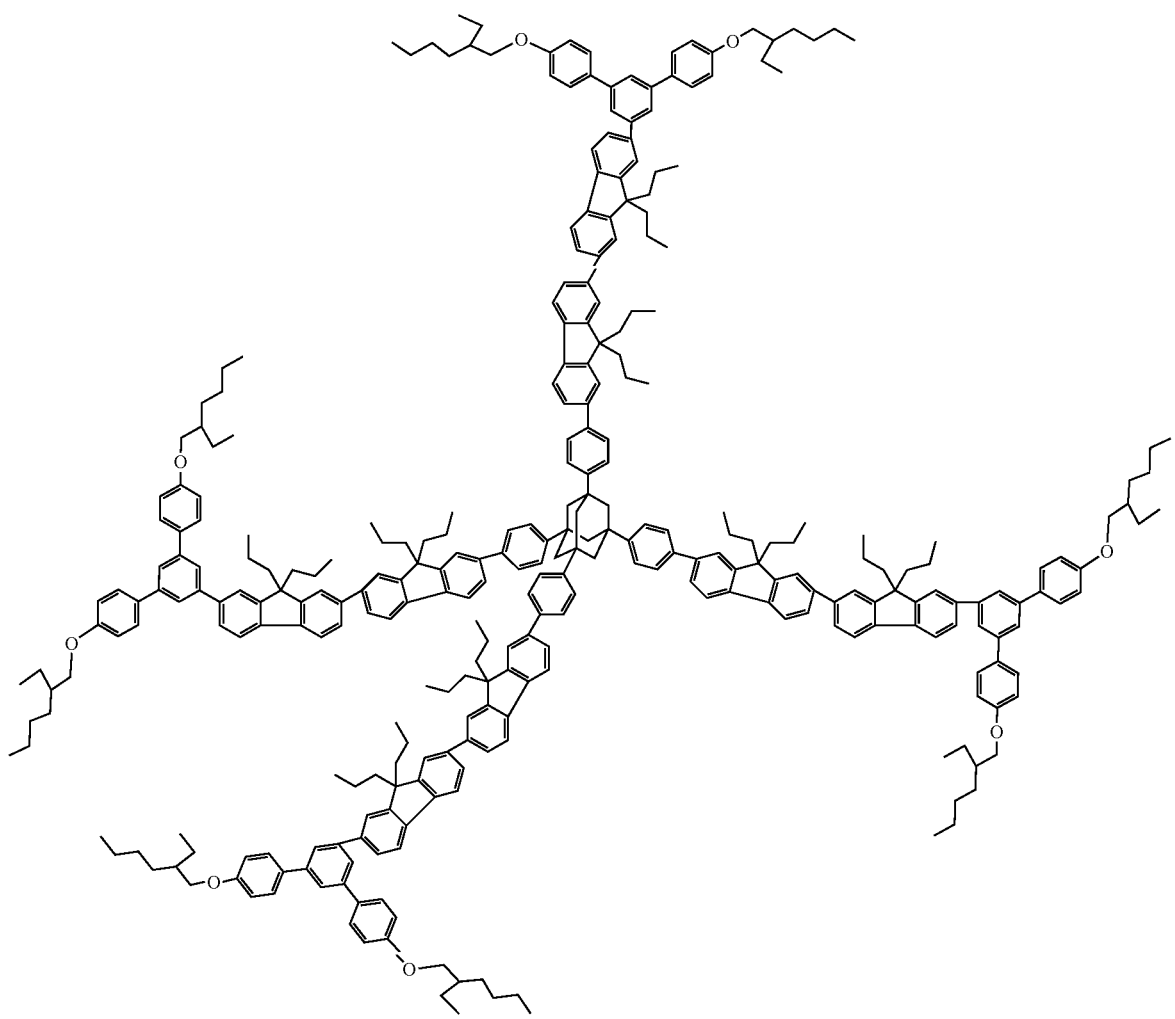

4

4a (300 mg, 0.1094 mmol), 3,5-bis(4-ethylhexyloxyphenyl)phenylboronic acid (290 mg, 0.5468 mmol) and tetrakis(triphenylphosphine)palladium(0) (12.6 mg, 0.0109 mmol) were added to a round bottom flask and flushed with argon. Aqueous sodium carbonate (0.3 cm³), ethanol (0.3 cm³) and toluene (0.6 cm³) were added and the mixture was degassed and purged with argon three times before being stirred at reflux for 48 hrs. Toluene (20 cm³) was added and the layers were separated. The aqueous layer was extracted with toluene (20 cm³) and the combined organic layers were washed with brine (20 cm³), dried over anhydrous magnesium sulfate, filtered and the solvent was removed to give a brown solid. The solid was purified by column chromatography over silica using a light-petroleum/dichloromethane mixture (10:0 to 10:2) as eluent. This gave a white solid which was then further purified by precipitation from a dichloromethane/methanol mixture to give 4 (0.297 g, 62%), mp 200-205° C.; (Found; C, 88.46; H, 8.48. $C_{322}H_{368}O_8$ requires; C, 88.57; H, 8.49%); $\delta_H$ (400 MHz; CDCl$_3$) 0.47-1.15 (120H), 1.15-1.55 (72H), 1.59-1.90 (24H), 1.91-2.21 (36H), 2.22-2.60 (8H), 6.96-7.11 (16H), 7.29-8.19 (92H).

Example 8

Measurements of Thin Films

Thin films were prepared by spin coating solutions of the compounds prepared in the above examples onto glass slides at a concentration of 20 mg/mL at 2000 rpm, which give films of approximately 100 nm thick. Photoluminescence (PL) was measured using a fibre optic detector after exciting the films with a UV lamp at 365 nm. Fluorescence quenching was then monitored after exposing the films to 1,4-dinitrobenzene (pDNB) in a chamber at room temperature and pressure. The vapour pressure of pDNB ($5.13 \times 10^{-6}$ atm) is 18 times that of TNT, and both molecules have the same reduction potential ($E_{red}$–0.7 V). Exposing the films in a stream of nitrogen promoted the recovery of fluorescence, indicating the diffusion of pDNB out of the film.

Sensing of pDNB with 1 is evidenced by the decrease of PL intensity after exposure to 1-3 hours. The PL was recovered by placing the film under nitrogen. Compound 2 showed 45% PL decrease after 1 h pDNB exposure, in comparison to 25% in 1. Compounds 3 and 4 showed a more rapid PL decrease (75% and 85%, respectively) on the same time scale, owing to the dimensionality of the compounds. Compounds 3 and 4 also showed quick recovery of PL after exposure to $N_2$ stream for 1 hour. These results support the concept that increasing the internal free volume of the compounds and/or increasing the external intermolecular space between molecules of the compounds used in the invention may promote sensitivity. Adding dimensionality to the compounds should increase the volume not only within the internal of the dendrimer, but also the external inter-molecular space. Larger molecules with poorer packing will give larger volumes of space in its solid-state which allow room for small molecules to diffuse.

Example 9

Effects of pDNB on the Lasing Performance of 1

The laser was fabricated from a solution of dendrimer 1 described in Example 1 of concentration 25 mg/ml in chloroform, spin-coated onto a corrugated silica substrate. The corrugation was 2-dimensional with a period $\Lambda$=260 nm in both directions. The grating was sinusoidal with an approximate peak to trough depth of 30 nm.

Figure 5:
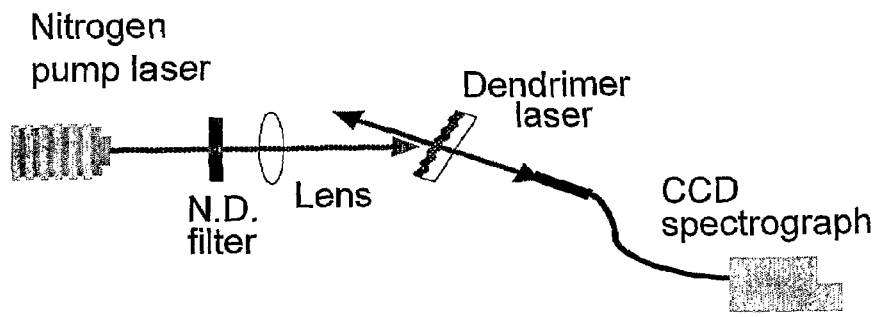
FIG. 5 is a schematic diagram showing lasing apparatus used in an example of the invention.

The sample was mounted in ambient conditions on a translation stage that could be moved in x, y and z coordinates. The mount consisted of a rotational bezel which clamped at the desired angle, away from normal incidence to prevent reflections along the beam path. The dendrimer laser was pumped with the 337 nm output of a N2 laser at a repetition rate of 10 Hz. Alignment was trivial due to the grating covering >90% of the surface area. The output through the substrate was collected using a fibre coupled CCD spectrometer of resolution ~0.6 nm. Attenuation of the pump beam was performed using reflective neutral density filters. A schematic showing the experimental set-up can be found in FIG. 5.

After initial characterisation of the unexposed sample, the sample and its mount were detached from the stage and moved to a fume cupboard. The sample was placed in proximity but not in contact with DNB crystals. A 400 ml glass beaker was used to limit the volume the DNB vapour could escape into. After one hour, the mount was reattached to the stage in its previous position and the laser was characterised a second time.

Finally, the mount and the sample were placed in a glove box, maintained under a nitrogen atmosphere for 16 hours to allow recovery of dendrimer 1. After this time, the mount was again attached to the stage in its original position and the experiment was performed for a third time.

Figure 6:
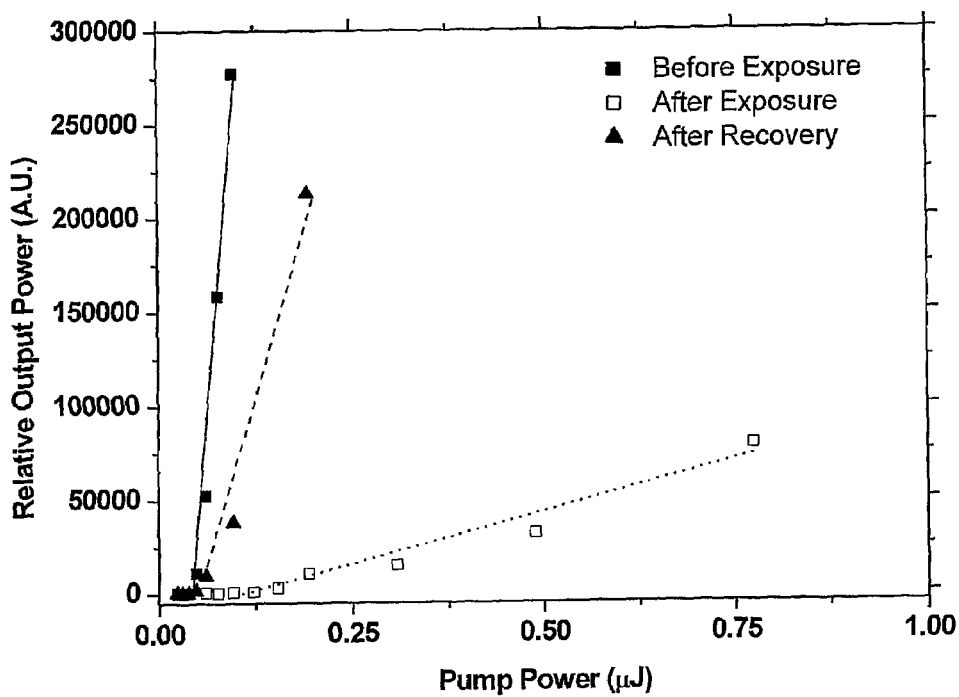
FIG. 6 shows lasing of 1 on a corrugated structure before exposure to pDNB, after exposure to pDNB, and after the pDNB was removed.

FIG. 6 shows the results for the lasing experiments for the sample before (filled squares) and after (open squares) exposure. The filled triangles show the performance of the dendrimer laser after it had been placed in nitrogen to recover. The graph shows the relative output intensities of the three stages (y axis) as a function of the input (pump) power from the nitrogen laser (x axis). The data for each of the three experiments show a relatively flat portion of the curve at low pump intensities corresponding to the device operating below the lasing threshold. This gives way to a rapid linear increase of output power with increasing input power as lasing threshold is achieved. The threshold for the device operating in each stage is provided in table 1.

TABLE 1

| | PL measurements | | Laser measurements | | |
|---|---|---|---|---|---|
| Sample | Relative Slope Efficiency | Output Power @ 0.1 µJ (Normalised) | Threshold (µJ) | Relative Slope Efficiency | Output Power @ 0.1 µJ (Normalised) |
| Before exposure | 1 | 1 | 0.04 | 1 | 1 |
| After exposure | 0.7 | 0.54 | 0.14 | 0.022 | 0.003 |
| After recovery | 0.9 | 0.97 | 0.045 | 0.27 | 0.13 |

The efficiency of this lasing can be determined from the gradient of the data above threshold, which is marked on FIG. 6 with solid (before exposure), dotted (after exposure) and dashed (after recovery) lines respectively. It can readily be seen, exposure of the laser based on dendrimer 1 to DNB has a dramatic effect upon the lasing output of the device. It can also be seen that prolonged exposure to nitrogen can help the device recover much of its initial optical properties.

Figure 7:
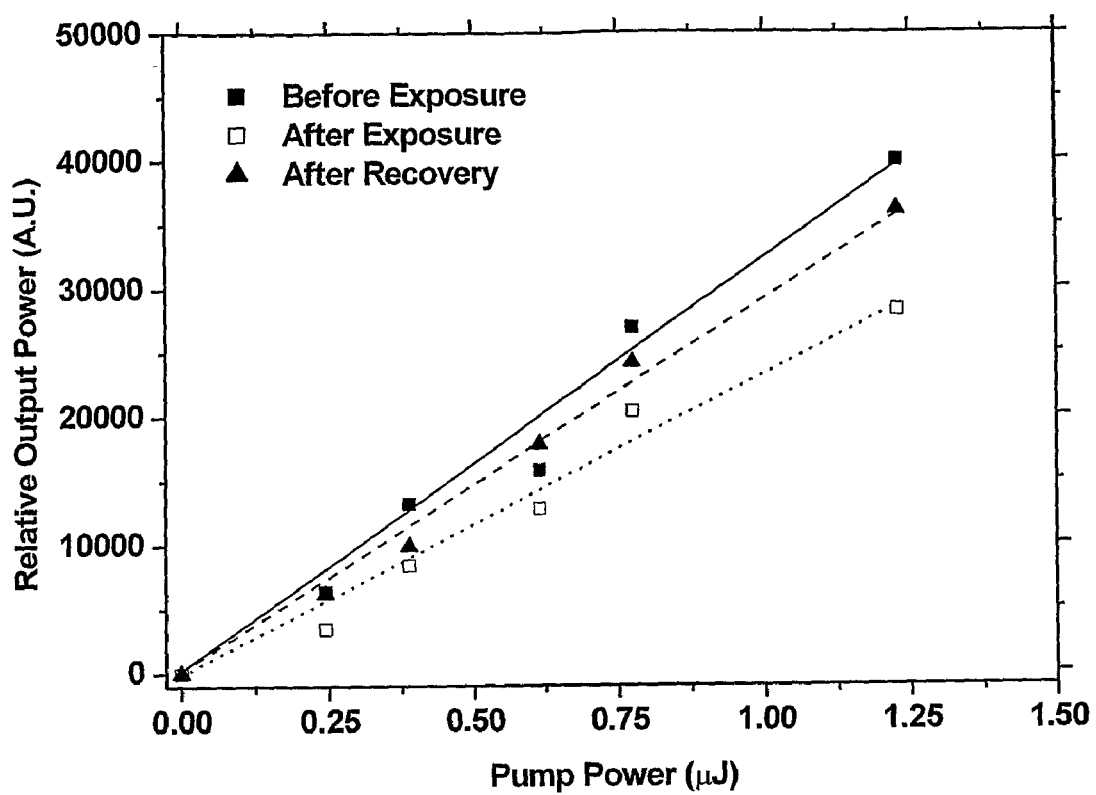
FIG. 7 shows the photoluminescence emission intensity as a function of input power change for 1 on a planar substrate for one cycle of exposure to pDNB.

As a comparison, a similar experiment was carried out upon a film of dendrimer 1 spin-coated onto a non-corrugated substrate in order to characterise the photoluminescence (PL) properties of the film when exposed to DNB. The result of this experiment is shown in FIG. 7. As can be seen, the overall trend of the device is the same as in the lasing experiment (FIG. 6), where exposure to the DNB causes a reduction in PL compared to the initial experiment. Here however, when the device is operating in a non lasing regime, the relative change in device efficiency is far less, indicating that the biggest sensitivity gains can be had when running the dendrimer 1 film in a lasing configuration.

This comparison can be best described through table 1 which states the relative efficiencies of the devices when operating with (lasing) and without (PL) the grating.

The relative slope efficiency is a measure of the gradient of the data above threshold (output power/input power) and has been normalised with respect to the device operating before exposure. It can be seen that when measuring the PL output of the dendrimer 1 film, the efficiency drops from 1 to 0.7 after exposure. In contrast, the laser device drops from 1 to 0.022, or almost 50 times as opposed to 1.4 times in the case of PL alone. Another way of expressing this result is that the output efficiency drops by 32 times more for the laser than for the PL device.

When the output is measured for a pump energy close to threshold, an even greater difference is observed after exposure. The column "output power at 0.1 µJ" gives the relative power from the device for a fixed input power, again normalised with respect to the output of the unexposed device. In the case of the PL, the output power at a pump energy of 0.1 µJ falls by half. However, for the laser, the exposure of the film to DNB has not only reduced the efficiency of the device, but increased the threshold. At a pump energy of 0.1 µJ, the unexposed sample has already begun lasing while the exposed sample is still operating below threshold. This leads to a difference between output powers of over 300 times, demonstrating the increased sensitivity of the lasing sample over the PL sample.

The invention claimed is:
1. A sensor comprising:
(i) a compound of formula (I):

[DENDRON$^1$]$_p$-CORE-[[X]$_r$[DENDRON]$_m$]$_n$  (I)

wherein
n is an integer of from 1 to 10;
p is zero or an integer of from 1 to 9;
the sum of n and p is from 3 to 10;
CORE is a group providing at least (n+p) points of attachment, each point of attachment being bonded to one X, DENDRON or DENDRON$^1$ group, and wherein the bonds between CORE and at least three X, DENDRON or DENDRON$^1$ groups are not coplanar;
each r is independently zero or an integer of from 1 to 10;
each m is independently zero or 1, with the proviso that for every point of attachment, when r is zero then m is one, and when m is zero then r is greater than zero;
each [X]$_r$ group is the same or different, wherein:
when m is zero, then –[X]$_r$ is a terminal group, and each X, which is the same or different if r is greater than one, is a group selected from aryl, heteroaryl, vinylene, acetylene and iptycene groups and from planar metal complexes;
when m is 1, then -[X]$_r$- is a linking group bonded to the CORE and terminating in a single bond to the first branching group of DENDRON, and each X, which is the same or different if r is greater than one, is a group selected from aryl, heteroaryl, vinylene, acetylene and iptycene groups and from planar metal complexes;
each DENDRON is the same or different and represents an at least partially conjugated dendritic molecular structure comprising at least one branching group and optionally at least one linking group, the branching groups being selected from aryl and heteroaryl groups and nitrogen atoms, and the linking groups being selected from aryl, heteroaryl, vinyl and acetylenyl groups, said branching groups being bonded to three or more groups, and said linking groups being bonded to two groups, said dendritic molecular structure terminating at its distal points in aryl and/or heteroaryl groups; and
each DENDRON$^1$, where present, represents an at least partially dendritic molecular structure,
wherein the compound of formula (I) is present in the sensor in the form of a film consisting essentially of said compound; and
(ii) an excitation source and detector capable of measuring the electronic and/or optical properties of the compound of formula (I).

2. A sensor as claimed in claim 1 wherein n is from 4 to 8.

3. A sensor as claimed in claim 2 wherein n is 4.

4. A sensor as claimed in claim 1 wherein each m is the same.

5. A sensor as claimed in claim 1 wherein p is zero.

6. A sensor as claimed in claim 1 wherein r is an integer of from 2 to 5 and each X is the same or different and represents a monocyclic aryl or heteroaryl group.

7. A sensor as claimed in claim 1 wherein r is an integer of from 1 to 5 and each X is the same or different and represents a polycyclic aryl or heteroaryl group.

8. A sensor as claimed in claim 1 wherein each X is selected from phenyl, naphthyl, anthracenyl, fluorenyl, pyridine and thiophene, said groups being optionally linked by vinylene and/or acetylene groups, and said groups being joined in series and being unsubstituted or substituted by one or more groups selected from $C_{1-10}$ alkyl and $C_{1-10}$ alkoxy.

9. A sensor as claimed in claim 8 wherein -[X]$_r$-comprises three aryl groups in series and selected from phenyl and fluorenyl, said phenyl and fluorenyl groups being unsubstituted or substituted by from one to three $C_{1-4}$ alkyl groups.

10. A sensor as claimed in claim 1 wherein at least one m is one, and wherein each DENDRON, which are the same or different if more than one is present, represents an at least partially conjugated dendritic molecular structure comprising at least one branching group and optionally at least one linking group, the branching groups being selected from aryl and heteroaryl groups, and the linking groups being selected from aryl, heteroaryl, vinyl and acetylenyl groups, said branching groups being bonded to three or more groups, and said linking groups being bonded to two groups, said dendritic molecular structure terminating at its distal points in aryl groups which are unsubstituted or substituted.

11. A sensor as claimed in claim 1 wherein the film is deposited onto a patterned substrate.

12. A sensor as claimed in claim 1 where the film of the compound of formula (I) or formula (II) is patterned by soft lithography.

13. A sensor as claimed in claim 1 wherein the film of the compound of formula (I) or formula (II) lases.

14. A sensor as claimed in claim 1 wherein the excitation source and detector are capable of measuring an optical property of the compound.

15. A sensor as claimed in claim 14 wherein the optical property is luminescence of the compound.

16. A sensor as claimed in claim 1 wherein the excitation source and detector are capable of measuring an electronic property of the compound.

17. A sensor as claimed in claim 16 wherein the sensor is a field effect transistor.

18. A method of detecting the presence of a target analyte in a test substance which method comprises:
(i) providing a film consisting essentially of a compound of formula (I) as defined in claim 1 and measuring the electronic and/or optical properties of said compound;
(ii) exposing said film to the test substance and measuring the electronic and/or optical properties of the compound following exposure to the test substance;
(iii) comparing the electronic and/or optical properties obtained in step (ii) with those obtained in step (i); and
(iv) determining that the target analyte is present if the electronic and/or optical properties obtained in step (ii) are different from those obtained in step (i).

19. A method as claimed in claim 18 wherein the target analyte is an explosive.

20. A sensor comprising:
(i) a compound of formula (II):

[DENDRON$^1$]$_p$-[X][DENDRON]$_q$  (II)

wherein:
q is an integer of from 1 to 10;
p is zero or an integer of from 1 to 9;
the sum of p and q is from 2 to 10;
r is zero or an integer of from 1 to 10;
-[X]$_r$- is a linker group between the two or more DENDRON or DENDRON$^1$ groups and providing at least (p+q) points of attachment, each point of attachment being bonded to a DENDRON or DENDRON$^1$ group;

each X, which is the same or different if r is greater than one, represents a group selected from aryl, heteroaryl, vinylene and acetylene groups and from planar metal complexes;

each DENDRON is the same or different and represents an at least partially conjugated dendritic molecular structure comprising at least one branching group and optionally at least one linking group, the branching groups being selected from aryl and heteroaryl groups and nitrogen atoms, and the linking groups being selected from aryl, heteroaryl, vinyl and acetylenyl groups, said branching groups being bonded to three or more groups, and said linking groups being bonded to two groups, said dendritic molecular structure terminating at its distal points in aryl and/or heteroaryl groups; and each DENDRON$^1$, where present, represents an at least partially dendritic molecular structure;

wherein the compound of formula (II) is present in the sensor in the form of a film consisting essentially of said compound; and (ii) an excitation source and detector capable measuring the electronic and/or optical properties of the compound of formula (II).

21. A sensor as claimed in claim 20 wherein q is from one to six.

22. A sensor as claimed in claim 20 wherein p is zero, one or two.

23. A sensor as claimed in claim 20 wherein each DENDRON, which is the same or different, represents an at least partially conjugated dendritic molecular structure comprising at least one branching group and optionally at least one linking group, the branching groups being selected from aryl and heteroaryl groups, and the linking groups being selected from aryl, heteroaryl, vinyl and acetylenyl groups, said branching groups being bonded to three or more groups, and said linking groups being bonded to two groups, said dendritic molecular structure terminating at its distal points in aryl groups which are unsubstituted or substituted.

* * * * *